(12) United States Patent
Brunet et al.

(10) Patent No.: US 7,863,328 B2
(45) Date of Patent: Jan. 4, 2011

(54) PHENYLBENZOIC ACID DERIVATIVES, PROCESSES FOR THE PREPARATION THEREOF, PHARMACEUTICAL COMPOSITIONS COMPRISING THEM, AND THERAPEUTIC USES THEREOF

(75) Inventors: Michel Brunet, Toussieu (FR); Nathalie Adje, Genas (FR); Valérie Guyard-Dangremont, Saint Maurice de Gourdans (FR); Francis Contard, Lyons (FR)

(73) Assignee: Merck Patent GmbH, Darmstadt (DE)

( * ) Notice: Subject to any disclaimer, the term of this patent is extended or adjusted under 35 U.S.C. 154(b) by 36 days.

(21) Appl. No.: 11/813,926

(22) PCT Filed: Dec. 22, 2005

(86) PCT No.: PCT/EP2005/013856

§ 371 (c)(1),
(2), (4) Date: Jul. 13, 2007

(87) PCT Pub. No.: WO2006/074796

PCT Pub. Date: Jul. 20, 2006

(65) Prior Publication Data

US 2008/0139599 A1 Jun. 12, 2008

(30) Foreign Application Priority Data

Jan. 14, 2005 (FR) ................................. 05 00421

(51) Int. Cl.
| | |
|---|---|
| *A61K 31/015* | (2006.01) |
| *A61K 31/16* | (2006.01) |
| *A61K 31/19* | (2006.01) |
| *A61K 31/216* | (2006.01) |
| *C07C 69/003* | (2006.01) |
| *C07C 63/06* | (2006.01) |
| *C07C 237/30* | (2006.01) |

(52) U.S. Cl. ...................... 514/546; 514/568; 514/617; 560/8; 562/492; 564/161

(58) Field of Classification Search ....................... 560/8
See application file for complete search history.

(56) References Cited

U.S. PATENT DOCUMENTS

2006/0276456 A1 12/2006 Wyeth

FOREIGN PATENT DOCUMENTS

| EP | 0885869 A | 12/1998 |
|---|---|---|
| WO | WO 02083145 A | 10/2002 |

OTHER PUBLICATIONS

Vippagunta, et al. Advanced Drug Delivery Reviews 2001 48 3-26.*
Mackay, et al. retrieved from CAPLUS on Nov. 6, 2008.*
Diabetes Guide [online], [retrieved from the internet on Jun. 17, 2008] [URL; http://diabetes.webmd.com/guide/diabetes-overview.*
Diabetes [online], [retrieved on Jun. 4, 2009] [retrieved from internet] URL; http://www.healthline.com/adamcontent/diabetes.*
RN 5728-32-5, CAPLUS, [retrieved on Jun. 4, 2009].*
RN 107517-12-4, CAPLUS, [retrieved on Jun. 4, 2009].*
Medrano, et al. Biochemistry 1989, 28, 5589-5599.*
Database Beilstein, Beilstein Institut Zur Foerderung Der Chemischen Wissenschaften; Frankfurt am Main; DE; XP002348879; Database Accession No. BRN 2108832 abstract & DE 23 29 125 A 1974.
Database Beilstein, Beilstein Institut Zur Foerderung Der Chemischen Wissenschaften; Frankfurt am Main; DE; XP002348880; Database Accession No. BRN2695461 abstract & J.Chem .Soc.Perkin Trans. 2, vol. 1, 1984, pp. 35-38.
Database Beilstein, Beilstein Institut Zur Foerderung Der Chemischen Wissenschaften; Frankfurt am Main; DE; XP002348881; Database Accession No. BRN3316063 abstract.
Database Beilstein, Beilstein Institut Zur Foerderung Der Chemischen Wissenschaften; Frankfurt am Main; DE; XP002348882; Database Accession No. BRN3363192 abstract & Bull.Chem.Soc.Jpn., vol. 32, 1959, p. 1292.
Database Beilstein, Beilstein Institut Zur Foerderung Der Chemischen Wissenschaften; Frankfurt am Main; DE; XP002348883; Database Accession No. BRN5192793 abstract & J.Chem .Soc.Perkin Trans. 2, 1982, pp. 1305-1308.
Database Beilstein, Beilstein Institut Zur Foerderung Der Chemischen Wissenschaften; Frankfurt am Main; DE; XP002348884; Database Accession No. BRN7638915 abstract & Larhed et al: Tetrahedron Lett., vol. 37, No. 45, 1996, pp. 8219-8222.

* cited by examiner

*Primary Examiner*—Rebecca L Anderson
*Assistant Examiner*—Shawquia Young
(74) *Attorney, Agent, or Firm*—Millen, White, Zelano & Branigan, P.C.

(57) ABSTRACT

Compounds of the formula (1) in which $R^1$, $R^2$, X, Y and Z are as defined in the description, the processes for the preparation of these compounds, the uses thereof for the treatment of dyslipidaemia, atherosclerosis and diabetes, and the pharmaceutical compositions comprising them.

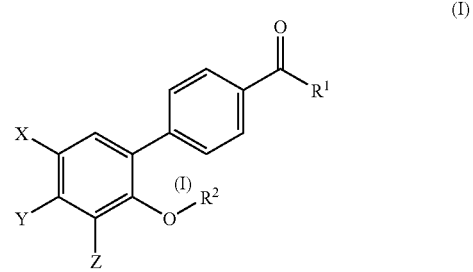

28 Claims, No Drawings

PHENYLBENZOIC ACID DERIVATIVES, PROCESSES FOR THE PREPARATION THEREOF, PHARMACEUTICAL COMPOSITIONS COMPRISING THEM, AND THERAPEUTIC USES THEREOF

The present invention relates to phenylbenzoic acid derivatives that can be used in the treatment of dyslipidaemia, atherosclerosis and diabetes. The invention also relates to pharmaceutical compositions comprising them and to processes for the preparation of these compounds.

In addition, the invention relates to the use of these compounds for the production of medicaments for the treatment of dyslipidaemia, atherosclerosis and diabetes.

The chronic effect of a calorie imbalance has resulted in an epidemic increase in the incidence of metabolic diseases in modern society. As a result, the World Health Organization has estimated that the global incidence of type 2 diabetes will exceed 300 million in 2030. Although several therapeutic options exist, none of them reverses the progress of this plague.

Although the control of glycated haemoglobin and plasmatic glycaemia in the fasted state are still considered as the primary objectives of antidiabetic treatments, acknowledgement of the fact that the diabetic state encompasses a range of metabolic disorders has broadened scope and expectations of future therapies. In the course of the last decade, hyperglycaemia has been shown to be not the only component of a series of anomalies affecting type-2 diabetic patients. Concurrent diseases, including insulin resistance, obesity, hypertension and dyslipidaemia, which, if they are present together or in part, constitutes what has been described as metabolic syndrome or syndrome X. This array of metabolic disorders forms the bases of a substantial increase in the incidence of cardiovascular disease in these patients.

In the search for novel and improved treatment options for diabetic patients, the family of receptors activated by the peroxisome proliferators ("peroxisome proliferator-activated receptor": PPAR) appears potentially to be an ideal target. This family of ligand-activated transcription factors modulates numerous aspects of lipid and carbohydrate metabolism, thus having the possibility of attacking several facets of the diabetic phenotype. There are three types of PPAR: PPAR alpha, gamma and delta (PPARα, PPARγ and PPARδ, respectively).

PPARα is involved in stimulating the β-oxidation of fatty acids. In rodents, a change transmitted by a PPARαin the expression of genes involved in fatty acid metabolism is the basis of the phenomenon of peroxisome proliferation, a pleiotropic cellular response, mainly limited to the liver and the kidneys, which can lead to hepatocarcinogenesis in rodents. The phenomenon of peroxisome proliferation is not encountered in man. In addition to its role in peroxisome proliferation in rodents, PPARα is also involved in controlling the levels of HDL cholesterol in rodents and humans. This effect is at least partially based on a transcription regulation transmitted by a PPARα of the major HDL apolipoproteins, apo A-I and apo A-II. The hypotriglyceridaemiant action of fibrates and fatty acids also involves PPARα and can be summarised as follows: (i) increased lipolysis and clearance of the remaining particles, due to changes in the levels of lipoprotein lipase and of apo C-III, (ii) stimulation of fatty acid uptake by the cell and its subsequent conversion into acyl-CoA derivatives by induction of a protein for binding fatty acids and acyl-CoA synthase, (iii) induction of the β-oxidation pathways of fatty acids, (iv) reduction in the synthesis of fatty acids and triglycerides, and finally (v) reduction in the production of VLDL. As a result, both the improved catabolism of the triglyceride-rich particles and the reduced secretion of VLDL particles constitute mechanisms that contribute towards the hypolipidaemiant effect of fibrates.

Fibric acid derivatives, such as clofibrate, fenofibrate, benzafibrate, ciprofibrate, beclofibrate and etofibrate, and also gemfibrozil, each of which are PPARα ligands and/or activators, produce a substantial reduction in plasmatic triglycerides and also a certain increase in HDLs. The effects on LDL cholesterol are contradictory and may depend on the compound and/or the dyslipidaemic phenotype. For these reasons, this class of compounds was first used for the treatment of hypertriglyceridaemia (i.e. Fredrickson Type IV and V) and/or mixed hyperlipidaemia.

The activation of a PPARδ was initially reported as not being involved in the modulation of the levels of glucose or of triglycerides (Berger et al., *J. Biol. Chem.*, (1999), Vol. 274, pp. 6718-6725). Later, it was shown that the activation of PPARδ leads to higher levels of HDL cholesterol in dbldb mice (Leibowitz et al., *FEBS Letters*, (2000), 473, 333-336). Furthermore, a PPARδ agonist, during its administration to obese adult insulin-resistant rhesus monkeys, caused a dramatic dose-dependent increase in HDL cholesterol in the serum, while at the same time reducing the levels of low-density LDLs, by depleting the triglycerides and the insulin (Oliver et al., *PNAS*, (2001), 98, 5306-5311). The same publication also showed that the activation of PPARδ increased the Al cassette binding the ATP inverse transporter of cholesterol and induced a flow of cholesterol specific for apolipoprotein A1. Taken together, these observations suggest that the activation of PPARδ is useful for the treatment of and preventing diseases and cardiovascular states comprising atherosclerosis, hypertriglyceridaemia and mixed dyslipidaemia (PCT publication WO 01/00603 (Chao et al.)).

The subtypes of PPARγ receptor are involved in the activation of the programme of adipocyte differentiation and are not involved in the stimulation of peroxisome proliferation in the liver. There are two known isoforms of PPARγ protein: PPARγ1 and PPARγ2, which differ only in the fact that PPARγ2 contains 28 additional amino acids at the amino end. The DNA sequences for the human isotypes are described by Elbrecht et al., *BBRC*, 224, (1996), 431-437. In mice, PPARγ2 is specifically expressed in the fat cells. Tontonoz et al., *Cell*, 79, (1994), 1147-1156, provide proof showing that one physiological role of PPARγ2 is to induce adipocyte differentiation. As with other members of the superfamily of nuclear hormone receptors, PPARγ2 regulates the expression of genes via an interaction with other proteins and binding to hormone response elements, for example in the 5' lateral regions of the response genes. An example of a PPARγ2 response gene is the tissue-specific P2 adipocyte gene. Although peroxisome proliferators, comprising fibrates and fatty acids, activate the transcriptional activity of PPAR receptors, only prostaglandin $J_2$ derivatives have been identified as potential natural ligands of the PPARγ subtype, which also binds antidiabetic thiazolidinedione agents with high affinity.

It is generally thought that glitazones exert their effects by binding to receptors of the family of peroxisome proliferator-activated receptors (PPAR), by controlling certain transcription elements in relation with the biological species listed above. See Hulin et al., *Current Pharm. Design*, (1996), 2, 85-102. In particular, PPARγ has been imputed as a major molecular target for the glitazone class of insulin sensitisers.

Many compounds of glitazone type, which are PPAR agonists, have been approved for use in the treatment of diabetes.

These are troglitazone, rosiglitazone and pioglitazone, which are all primary or exclusive agonists of PPARγ.

This indicates that the search for compounds having varying degrees of PPARα, PPARγ and PPARδ activation might lead to the discovery of medicaments that efficiently reduce triglycerides and/or cholesterol and/or glucose, presenting great potential in the treatment of diseases, such as type 2 diabetes, dyslipidaemia, syndrome X (comprising metabolic syndrome, i.e. reduced glucose tolerance, insulin resistance, hypertriglyceridaemia and/or obesity), cardiovascular diseases (comprising atherosclerosis) and hypercholesterolaemia.

The combinations of the PPAR activities that have been studied the most extensively are the PPAR alpha plus gamma combination (dual agonists) with, especially, tesaglitazar, and also the alpha, gamma plus delta triple combination (PPAR-pan agonists).

Although glitazones are beneficial in the treatment of NIDDM, a number of serious unfavourable side effects associated with the use of these compounds have been found. The most serious of these was toxicity to the liver, which has resulted in a certain number of deaths. The most serious problems arose in the use of troglitazone, which has recently been removed from the market for toxicity reasons.

Besides the potential hepatic toxicity of glitazones, other deleterious effects have been associated with PPAR gamma full agonists, for instance weight gain, anaemia and oedema, which limit their use (rosiglitazone, pioglitazone).

On account of the problems that have been encountered with glitazones, researchers in many laboratories have studied classes of PPAR agonists that are not glitazones and do not contain 1,3-thiazolidinedione species, but which modulate the three known subtypes of PPAR, together or separately, to variable degrees (measured by intrinsic power, maximum breadth of functional response or spectrum of changes in gene expression).

Thus, recent studies (cf. WO 01/30343 and WO 02/08188) have revealed that certain compounds have PPAR agonist or partial agonist properties, which are useful in the treatment of type 2 diabetes with reduced side effects with respect to the heart weight and body weight.

The inventors have now discovered a novel class of compounds that are partial or full agonists of PPARγ, with differing degrees of PPARα and/or PPARδ activity.

More specifically, the invention relates to phenylbenzoic acid-based compounds of the formula (1) below:

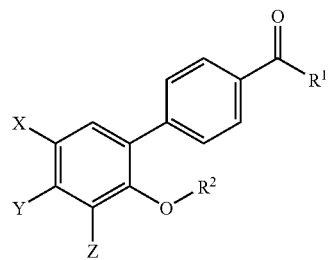

(1)

in which:
R$^1$ represents —O—R'$^1$ or —NR'$^1$R'''$^1$, with R'$^1$ and R'''$^1$, which may be identical or different, being chosen from a hydrogen atom, an alkyl radical, an alkenyl radical, an alkynyl radical, a cycloalkyl radical, an aryl radical and a heteroaryl radical;

R$^2$ is chosen from:
an alkyl, alkenyl or alkynyl radical;
an optionally substituted arylalkyl radical; and
an optionally substituted heterocyclylalkyl radical;
[lacuna] is chosen from an oxygen atom and a sulfur atom; and
X, Y and Z, which may be identical or different, are chosen, independently of each other, from a hydrogen atom, a halogen atom, an alkyl radical and an alkoxy radical; or alternatively X and Y together form, with the carbon atoms that bear them, a 5-membered ring containing a ketone function;
the possible optical isomers, oxide forms and solvates thereof, and also the pharmaceutically acceptable addition salts thereof with acids or bases.

The acids that can be used for the formation of salts of compounds of the formula (1) are mineral or organic acids. The resulting salts are, for example, the hydrochlorides, hydrobromides, sulfates, hydrogen sulfates, dihydrogen phosphates, citrates, maleates, fumarates, trifluoroacetates, 2-naphthalenesulfonates and para-toluenesulfonates.

The bases that can be used for the formation of salts of compounds of the formula (1) are organic or mineral bases. The resulting salts are, for example, the salts formed with metals and especially alkali metals, alkaline-earth metals and transition metals (such as sodium, potassium, calcium, magnesium or aluminium) or with bases, for instance ammonia or secondary or tertiary amines (such as diethylamine, triethylamine, piperidine, piperazine or morpholine) or with basic amino acids, or with osamines (such as meglumine) or with amino alcohols (such as 3-aminobutanol and 2-aminoethanol).

The invention especially encompasses the pharmaceutically acceptable salts, but also salts that allow a suitable separation or crystallisation of the compounds of the formula (1), such as the salts obtained with chiral amines or chiral acids.

Examples of chiral amines that can be used include quinine, brucine, (S)-1-(benzyloxymethyl)propylamine (III), (–)-ephedrine, (4S,5R)-(+)-1,2,3,4-tetramethyl-5-phenyl-1,3-oxazolidine, (R)-1-phenyl-2-p-tolylethyl-amine, (S)-phenylglycinol, (–)-N-methylephedrine, (+)-(2S,3R)-4-dimethyl-amino-3-methyl-1,2-diphenyl-2-butanol, (S)-phenylglycinol and (S)-α-methyl-benzylamine, or a mixture of two or more thereof.

Examples of chiral acids that can be used include (+)-d-di-O-benzoyltartaric acid, (–)-l-di-O-benzoyltartaric acid, (–)-di-O,O'-p-toluyl-l-tartaric acid, (+)-di-O,O'-p-toluyl-d-tartaric acid, (R)-(+)-malic acid, (S)-(–)-malic acid, (+)-camphanic acid, (–)-camphanic acid, R-(–)-1,1'-binaphthalene-2,2'-diyl hydrogen phosphate, (S)-(+)-1,1'-binaphthalene-2,2'-diyl hydrogen phosphate, (+)-camphoric acid, (–)-camphoric acid, (S)-(+)-2-phenylpropionic acid, (R)-(–)-2-phenylpropionic acid, d-(–)-mandelic acid, l-(+)-mandelic acid, d-tartaric acid and l-tartaric acid, or a mixture of two or more thereof.

The chiral acid is preferably chosen from (–)-di-O,O'-p-toluyl-l-tartaric acid, (+)-di-O,O'-p-toluyl-d-tartaric acid, (R)-(–)-1,1'-binaphthalene-2,2'-diyl hydrogen phosphate, (S)-(+)-1,1'-binaphthalene-2,2'-diyl hydrogen phosphate, d-tartaric acid and L-tartaric acid, or a mixture of two or more thereof.

The invention also encompasses the possible optical isomers, in particular stereoisomers and diastereoisomers, where appropriate, of the compounds of the formula (1), and also mixtures of the optical isomers in any proportions, including racemic mixtures.

Depending on the nature of the substituents, the compounds of the formula (1) may also be in various tautomeric forms, which are also included in the present invention, alone or as mixtures of two or more thereof, in all proportions.

The compounds of the formula (1) above also include the prodrugs of these compounds.

The term "prodrugs" means compounds which, once administered to the patient, are chemically and/or biologically converted by the living body, into compounds of the formula (1).

In the compounds of the formula (1) defined above, the term "alkyl radical" means a linear or branched hydrocarbon-based chain containing from 1 to 10 carbon atoms and better still from 1 to 6 carbon atoms, for example from 1 to 4 carbon atoms.

Examples of alkyl radicals are methyl, ethyl, propyl, isopropyl, butyl, isobutyl, tert-butyl, pentyl, isopentyl, neopentyl, 2-methylbutyl, 1-ethyl-propyl, hexyl, isohexyl, neohexyl, 1-methylpentyl, 3-methylpentyl, 1,1-dimethylbutyl, 1,3-dimethylbutyl, 1-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyl-octyl and 7,7-dimethyloctyl, preferably methyl, ethyl, propyl, isopropyl, butyl, isobutyl, tert-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 1-ethylbutyl, 1-methyl-1-ethylpropyl, more preferably methyl, ethyl, propyl, isopropyl, butyl, isobutyl, tert-butyl The alkyl radicals present as substituents of the compounds of the formula (1) according to the present invention may be optionally substituted by one or more chemical species chosen from:
halogen atom;
—O-alkyl radical;
aryl radical;
cycloalkyl radical; and
heterocyclic radical.

The term "alkoxy" refers to a radical alkyl-O—, in which the term "alkyl" has all the characteristics defined above.

The term "arylalkyl" denotes a radical in which the alkyl portion is as defined above and the aryl portion denotes a monocyclic or polycyclic carbocyclic aromatic radical containing from 6 to 18 carbon atoms and preferably from 6 to 10 carbon atoms. Aryl radicals that may be mentioned include phenyl, naphthyl, anthryl and phenanthryl radicals.

The term "alkenyl radical" means a linear or branched hydrocarbon-based chain containing from 2 to 10 carbon atoms, preferably from 2 to 8 carbon atoms and advantageously from 2 to 6 carbon atoms, containing one, two or more unsaturations in the form of a double bond, the said chain being optionally substituted by one or more substituents, which may be identical or different, chosen from halogen atoms and trifluoromethyl, trifluoromethoxy, hydroxyl, alkoxy, alkoxycarbonyl, carboxyl and oxo radicals.

Examples of alkenyl radicals that may be mentioned include the ethylenyl radical, the propenyl radical, the isopropenyl radical, the but-2-enyl radical, pentenyl radicals and hexenyl radicals.

The term "alkynyl radical" means a linear or branched hydrocarbon-based chain containing from 2 to 10 carbon atoms, preferably from 2 to 8 carbon atoms and advantageously from 2 to 6 carbon atoms, containing one, two or more unsaturations in the form of a triple bond, the said chain being optionally substituted by one or more substituents, which may be identical or different, chosen from halogen atoms and trifluoromethyl, trifluoromethoxy, hydroxyl, alkoxy, alkoxycarbonyl, carboxyl and oxo radicals.

Examples of alkynyl radicals that may be mentioned include the ethynyl radical, the propynyl radical, the but-2-ynyl radical, pentynyl radicals and hexynyl radicals.

In the present invention, the cycloalkyl radical is taken to mean a cyclic hydrocarbon-based radical containing from 4 to 9 carbon atoms, preferably 5, 6 or 7 carbon atoms and advantageously 5 or 6 carbon atoms, optionally containing one or more unsaturations in the form of double and/or triple bonds, the said cycloalkyl radical being optionally substituted by one or more substituents, which may be identical or different, chosen from halogen atoms and alkyl, alkenyl, alkynyl, trifluoromethyl, trifluoromethoxy, hydroxyl, alkoxy, alkoxycarbonyl, carboxyl and oxo radicals.

Preferred examples of cycloalkyl radicals are cyclobutyl, cyclopentyl, cyclopentenyl, cyclohexyl, cyclohexenyl, cyclohexadienyl, cycloheptyl, cycloheptenyl and cycloheptadienyl.

Unless otherwise indicated, the heterocyclic portion of the heterocyclylalkyl radicals corresponds to a saturated, unsaturated or aromatic, 5- to 8-membered heterocyclic radical containing one or more hetero atoms generally chosen from O, S and N, optionally in oxidised form (in the case of S and N), and optionally one or more unsaturations in the form of double bonds. If they are totally saturated, the heterocyclic radicals are said to be aromatic or heteroaryl radicals.

Preferably, at least one of the monocycles constituting the heterocycle contains from 1 to 4 endocyclic hetero atoms and better still from 1 to 3 hetero atoms.

Preferably, the heterocycle consists of one or more monocycles, each of which is 5- to 8-membered.

Examples of 5- to 8-membered monocyclic aromatic heterocyclic radicals are the heteroaryl radicals derived, by abstraction of a hydrogen atom, from aromatic heterocycles, such as pyridine, furan, thiophene, pyrrole, imidazole, thiazole, isoxazole, isothiazole, furazane, pyridazine, pyrimidine, pyrazine, thiazines, oxazole, pyrazole, oxadiazole, triazole and thiadiazole.

Preferred aromatic heterocyclic radicals that may be mentioned include pyridyl, pyrimidinyl, triazolyl, thiadiazolyl, oxazolyl, thiazolyl and thienyl radicals.

Examples of bicyclic heteroaryls in which each monocycle is 5- to 8-membered are chosen from indolizine, indole, isoindole, benzofuran, benzothiophene, indazole, benzimidazole, benzothiazole, benzofurazane, benzothiofurazane, purine, quinoline, isoquinoline, cinnoline, phthalazine, quinazoline, quinoxaline, naphthyridines, pyrazolotriazines (such as pyrazolo-1,3,4-triazine), pyrazolopyrimidine and pteridine.

Preferred heteroaryl radicals that may be mentioned include the quinolyl, pyridyl, benzothiazolyl and triazolyl radicals.

The tricyclic heteroaryls in which each monocycle is 5- to 8-membered are chosen, for example, from acridine, phenazine and carbazole.

Saturated or unsaturated, 5- to 8-membered monocyclic heterocycles are the saturated or, respectively, unsaturated derivatives of the aromatic heterocycles mentioned above.

More particularly, mention may be made of morpholine, piperidine, thiazolidine, oxazolidine, tetrahydrothienyl, tetrahydrofuryl, pyrrolidine, isoxazolidine, imidazolidine and pyrazolidine.

If the radicals defined above are qualified by "optionally substituted", they may contain one or more substituents chosen from halogen atom, alkyl radical, alkoxy radical, trifluoromethyl, trifluoromethoxy, styryl, monocyclic, bicyclic or tricyclic aromatic heterocyclic radical containing one or more hetero atoms chosen from O, N and S; and optionally substituted by one or more radicals T as defined below; group Het-CO— in which Het represents an aromatic heterocyclic radical as defined above, optionally substituted by one or more radicals T; a $C_1$-$C_6$ alkylene chain; a $C_1$-$C_6$ alkylenedioxy chain; nitro; cyano; ($C_1$-$C_{10}$)alkyl; ($C_1$-$C_{10}$)alkylcarbonyl; ($C_1$-$C_{10}$)alkoxycarbonyl-A- in which A represents ($C_1$-$C_6$)alkylene, ($C_2$-$C_6$)alkenylene or a bond; ($C_3$-$C_{10}$)cycloalkyl; trifluoromethoxy; di($C_1$-$C_{10}$)alkylamino; ($C_1$-$C_{10}$) alkoxy($C_1$-$C_{10}$)alkyl; ($C_1$-$C_{10}$)alkoxy; ($C_6$-$C_{18}$)aryl optionally substituted by one or more radicals T; ($C_6$-$C_{18}$)aryl($C_1$-$C_{10}$)alkoxy(CO)$_n$— in which n is 0 or 1 and aryl is optionally substituted by one or more radicals T; ($C_6$-$C_{18}$)aryloxy-(CO)$_n$— in which n is 0 or 1 and aryl is optionally substituted by one or more radicals T; ($C_6$-$C_{18}$)arylthio in which aryl is optionally substituted by one or more radicals T; ($C_6$-$C_{18}$) aryloxy($C_1$-$C_{10}$)alkyl(CO)$_n$— in which n is 0 or 1 and aryl is optionally substituted by one or more radicals T; a saturated or unsaturated, 5- to 8-membered monocyclic heterocyclic or heterocyclylalkyl radical containing one or more hetero atoms chosen from O, N and S, optionally substituted by one or more radicals T; ($C_6$-$C_{18}$)arylcarbonyl optionally substituted by one or more radicals T; ($C_6$-$C_{18}$)arylcarbonyl-B-(CO)$_n$— in which n is 0 or 1; B represents ($C_1$-$C_6$)alkylene or ($C_2$-$C_6$)alkenylene and aryl is optionally substituted by one or more radicals T; ($C_6$-$C_{18}$)aryl-C-(CO)$_n$— in which n is 0 or 1, C represents ($C_1$-$C_6$)alkylene or ($C_2$-$C_6$)alkenylene and aryl is optionally substituted by one or more radicals T; ($C_6$-$C_{18}$) aryl fused with a saturated or unsaturated heterocycle as defined above, optionally substituted by one or more radicals T; and ($C_2$-$C_{10}$)alkynyl.

T is chosen from a halogen atom; ($C_6$-$C_{18}$)aryl; ($C_1$-$C_6$) alkyl; ($C_1$-$C_6$)alkoxy; ($C_1$-$C_6$)alkoxy($C_6$-$C_{18}$)aryl; nitro; carboxyl; ($C_1$-$C_6$)alkoxycarboxyl; and T may represent oxo if it substitutes a saturated or unsaturated heterocycle; or alternatively T represents ($C_1$-$C_6$)alkoxycarbonyl($C_1$-$C_6$)alkyl; or ($C_1$-$C_6$)alkylcarbonyl(($C_1$-$C_6$)alkyl)$_n$- in which n is 0 or 1.

The term "halogen atom" means a chlorine, bromine, iodine or fluorine atom, preferably fluorine or chlorine.

Among the compounds of the formula (1), the ones that are preferred are those for which $R^1$ represents —O—$R'^1$ and most particularly those for which $R^1$ represents —O—$R'^1$, $R'^1$ being a hydrogen atom or an alkyl radical.

A first preferred group of compounds of the invention consists of compounds having one or more of the following characteristics, taken separately or as a combination of one, several or all of them:
$R^1$ represents —O—$R'^1$, $R'^1$ being chosen from a hydrogen atom, an alkyl radical, an alkenyl radical, an alkynyl radical, a cycloalkyl radical, an aryl radical and a heteroaryl radical;
$R^2$ is chosen from an alkyl radical, an optionally substituted benzyl radical and an optionally substituted heterocyclylalkyl radical;
X and Y, which may be identical or different, are chosen, independently of each other, from a hydrogen atom, a halogen atom, an alkyl radical and an alkoxy radical; or alternatively X and Y together form, with the carbon atoms that bear them, a 5-membered ring containing a ketone function; and
Z is chosen from a hydrogen atom, a halogen atom, an alkyl radical and an alkoxy radical;
the possible optical isomers, oxide forms and solvates thereof, and also the pharmaceutically acceptable addition salts thereof with acids or bases.

Another even more preferred group of compounds of the invention consists of compounds having one or more of the following characteristics, taken separately or as a combination of one, several or all of them:
$R^1$ represents —O—$R'^1$, $R'^1$ being chosen from a hydrogen atom and an alkyl radical;
$R^2$ is chosen from an alkyl radical, an optionally substituted benzyl radical and an optionally substituted heterocyclylalkyl radical;
X and Y, which may be identical or different, are chosen, independently of each other, from a hydrogen atom, a halogen atom, an alkyl radical and an alkoxy radical; or alternatively X and Y together form, with the carbon atoms that bear them, a 5-membered ring containing a ketone function; and
Z is chosen from a hydrogen atom and a halogen atom;
the possible optical isomers, oxide forms and solvates thereof, and also the pharmaceutically acceptable addition salts thereof with acids or bases.

Another preferred group of compounds of the invention consists of compounds having one or more of the following characteristics, taken separately or as a combination of one, several or all of them:
$R^1$ represents —O—$R'^1$, $R'^1$ being chosen from a hydrogen atom, a methyl radical and an ethyl radical;
$R^2$ is chosen from an alkyl radical, an optionally substituted benzyl radical and an optionally substituted heterocyclylalkyl radical;
X and Y, which may be identical or different, are chosen, independently of each other, from a hydrogen atom, a fluorine atom, a chlorine atom, a methyl radical and a methoxy radical; or alternatively X and Y together form, with the carbon atoms that bear them, a cyclopentenone ring; and
Z is chosen from a hydrogen atom, a fluorine atom and a chlorine atom;
the possible optical isomers, oxide forms and solvates thereof, and also the pharmaceutically acceptable addition salts thereof with acids or bases.

The possible substituents on the radicals defined above for the compounds of the formula (1) are preferably chosen from halogen atoms, preferably fluorine and/or chlorine, and methyl, ethyl, methoxy, phenyl, trifluoromethyl and trifluoromethoxy radicals.

The heterocyclic radicals are preferentially chosen from furyl, thienyl, pyrrolyl, pyridyl, triazolyl, oxazolidinyl, thiazolyl, oxadiazolyl and oxazolyl radicals.

More particularly, the compounds of the formula (1) that are preferred are chosen from:
4-[6-(5-methyl-2-phenyloxazol-4-ylmethoxy)-1-oxoindan-5-yl]benzoic acid;
4-[1-oxo-6-(4-trifluoromethylbenzyloxy)indan-5-yl]benzoic acid;
4-[6-(2-fluorobenzyloxy)-1-oxoindan-5-yl]benzoic acid;
5'-methoxy-2'-(5-methyl-2-phenyloxazol-4-ylmethoxy) biphenyl-4-carboxylic acid;
5'-methyl-2'-(5-methyl-2-phenyloxazol-4-ylmethoxy)biphenyl-4-carboxylic acid;
4-[6-(5-methylisoxazol-3-ylmethoxy)-1-oxoindan-5-yl] benzoic acid;
4-[6-(5-methyl-2-phenyl-2H-[1,2,3]triazol-4-ylmethoxy)-1-oxoindan-5-yl]benzoic acid;
4-[1-oxo-6-(2-thiophen-2-ylthiazol-4-ylmethoxy)indan-5-yl]benzoic acid; and
4-[6-(5-methyl-3-phenylisoxazol-4-ylmethoxy)-1-oxoindan-5-yl]benzoic acid;
and from the possible optical isomers, oxide forms and solvates, and also the pharmaceutically acceptable addition salts with acids or bases, of these compounds.

The invention also relates to pharmaceutical compositions comprising a pharmaceutically effective amount of at least one compound of the formula (1) as defined above in combination with one or more pharmaceutically acceptable vehicles.

These compositions can be administered orally in the form of tablets, gel capsules or granules with immediate release or controlled release, intravenously in the form of an injectable solution, transdermally in the form of an adhesive transdermal device, or locally in the form of a solution, cream or gel.

A solid composition for oral administration is prepared by adding to the active principle a filler and, where appropriate, a binder, a disintegrant, a lubricant, a dye or a flavour enhancer, and by forming the mixture into a tablet, a coated tablet, a granule, a powder or a capsule.

Examples of fillers include lactose, corn starch, sucrose, glucose, sorbitol, crystalline cellulose and silicon dioxide, and examples of binders include poly(vinyl alcohol), poly(vinyl ether), ethylcellulose, methylcellulose, acacia, gum tragacanth, gelatine, shellac, hydroxypropylcellulose, hydroxypropylmethylcellulose, calcium citrate, dextrin and pectin. Examples of lubricants include magnesium stearate, talc, polyethylene glycol, silica and hardened plant oils. The dye can be any dye permitted for use in medicaments. Examples of flavour enhancers include cocoa powder, mint in herb form, aromatic powder, mint in oil form, borneol and cinnamon powder. Needless to say, the tablet or granule may be appropriately coated with sugar, gelatine or the like.

An injectable form comprising the compound of the present invention as active principle is prepared, where appropriate, by mixing the said compound with a pH regulator, a buffer, a suspending agent, a solubilising agent, a stabiliser, a tonicity agent and/or a preserving agent, and by converting the mixture into a form for intravenous, subcutaneous or intramuscular injection according to a standard process. Where appropriate, the injectable form obtained can be freeze-dried via a standard process.

Examples of suspending agents include methylcellulose, polysorbate 80, hydroxyethylcellulose, acacia, powdered gum tragacanth, sodium carboxymethyl cellulose and polyethoxylated sorbitan monolaurate.

Examples of solubilising agents include castor oil solidified with polyoxyethylene, polysorbate 80, nicotinamide, polyethoxylated sorbitan monolaurate and the ethyl ester of castor oil fatty acid.

In addition, the stabiliser encompasses sodium sulfite, sodium metasulfite and ether, while the preserving agent encompasses methyl p-hydroxybenzoate, ethyl p-hydroxybenzoate, sorbic acid, phenol, cresol and chlorocresol.

The present invention also relates to the use of a compound of the formula (1) of the invention for the preparation of a medicament for the prevention or treatment of dyslipidaemia, atherosclerosis and diabetes.

The effective administration doses and posologies of the compounds of the invention, intended for the prevention or treatment of a disease, condition or state caused by or associated with modulation of the activity of the PPARs, depends on a large number of factors, for example on the nature of the agonist, the size of the patient, the desired aim of the treatment, the nature of the pathology to be treated, the specific pharmaceutical composition used and the observations and conclusions of the treating doctor.

For example, in the case of an oral administration, for example, a tablet or a gel capsule, a possible suitable dosage of the compounds of the formula (1) is between about 0.1 mg/kg and about 100 mg/kg of body weight per day, preferably between about 0.5 mg/kg and about 50 mg/kg of body weight per day, more preferentially between about 1 mg/kg and about 10 mg/kg of body weight per day and more preferably between about 2 mg/kg and about 5 mg/kg of body weight per day of active material.

If representative body weights of 10 kg and 100 kg are considered in order to illustrate the daily oral dosage range that can be used and as described above, suitable dosages of the compounds of the formula (1) will be between about 1-10 mg and 1000-10 000 mg per day, preferably between about 5-50 mg and 500-5000 mg per day, more preferably between about 10.0-100.0 mg and 100.0-1000.0 mg per day and even more preferentially between about 20.0-200.0 mg and about 50.0-500.0 mg per day of active material comprising a preferred compound.

These dosage ranges represent total amounts of active material per day for a given patient. The number of administrations per day at which a dose is administered may vary within wide proportions as a function of pharmacokinetic and pharmacological factors, such as the half-life of the active material, which reflects its rate of catabolism and of clearance, and also the minimum and optimum levels of the said active material reached in the blood plasma or other bodily fluids of the patient and which are required for therapeutic efficacy.

Many other factors should also be considered in deciding upon the number of daily administrations and the amount of active material that should be administered at a time. Among these other factors, and not the least of which, is the individual response of the patient to be treated.

The present invention also relates to a general process for the preparation of the compounds of the formula (1) from a compound of the formula (2):

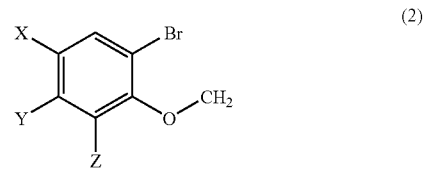

(2)

in which X, Y and Z are as defined above, which is subjected to the action of a boronic acid of the formula (3):

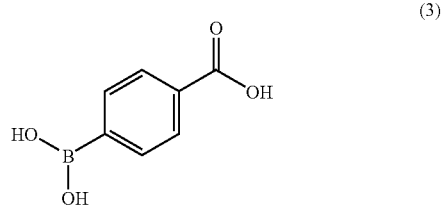

(3)

in the presence of a catalyst, such as a palladium (II) salt, for example bis(tricyclohexylphosphine)palladium(II) chloride, in the presence of hydrazinium hydroxide and trisodium phosphate, in polar protic medium, for example water, optionally in the presence of a co-solvent, for example tetrahydrofuran, to give the compound of the formula (4):

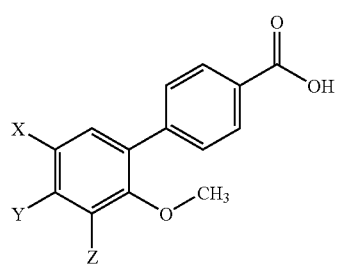

(4)

in which X, Y and Z are as defined above,
in which compound of the formula (4) the methoxy group is converted into an alcohol function, according to standard techniques, for example in the presence of a Lewis acid, for example aluminium trichloride, to give the compound of the formula (5):

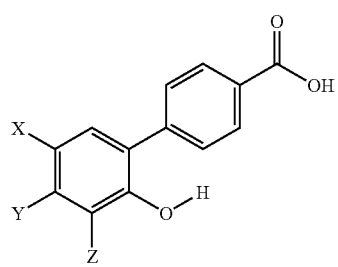

(5)

in which X, Y and Z are as defined above,
and then esterified, in order to protect the acid function, with an alcohol of the formula $R_A$—OH, in which $R_A$ represents a linear or branched alkyl radical containing from 1 to 4 carbon atoms, for example methanol, according to a usual procedure, for example in tetrahydrofuran, in the presence of a strong acid, such as sulfuric acid, to give the ester of the formula (6):

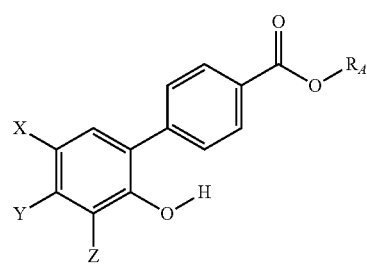

(6)

in which $R_A$, X, Y and Z are as defined above,
which compound of the formula (6) is then subjected to the action of a halide of the formula Hal-$R^2$, in which Hal represents a halogen atom, advantageously chlorine, bromine or iodine, preferably chlorine, and $R^2$ is as defined above,
in the presence of a base, such as an alkali metal carbonate, for example potassium carbonate or caesium carbonate, optionally in the presence of an activator, such as an alkali metal halide, for example potassium iodide, in polar aprotic medium, for example in acetone or dimethylformamide (DMF) solvent,
to give the compound of the formula (7):

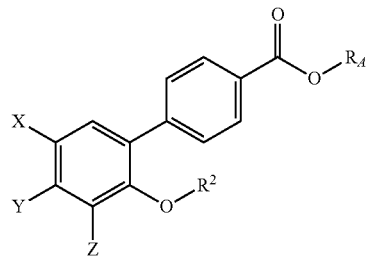

(7)

in which $R_A$, $R^2$, X, Y and Z are as defined above,
the protecting group $R_A$ of which is then removed, according to the standard techniques known to those skilled in the art, to give the acid of the formula ($1_{OH}$):

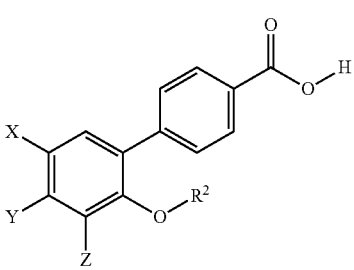

($1_{OH}$)

which is a special case of the compounds of the formula (1) in which $R^1$ represents a hydroxyl radical,
and the acid is optionally esterified, or converted into the corresponding amide, also according to standard techniques, to form the set of compounds of the formula (1), with $R^1$ other than a hydroxyl radical.

It should be understood that the compounds of the formula (7) above, if R represents an alkyl radical, form part of the compounds of the formula (1) according to the present invention.

If such compounds are desired, the steps of deprotection of the acid function and then of esterification are superfluous.

According to one variant, the compound of the formula (2a):

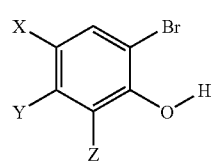

(2a)

in which X, Y and Z are as defined above,
which can be obtained according to standard processes known to those skilled in the art from the compound of the formula (2) defined above, can serve as starting compound for the formation of the compounds of the formula (1), by first introducing the radical $R^2$, under the action of the halide Hal-$R^2$ defined above, or alternatively of the alcohol OH—R² in the presence of a phosphine, in order to obtain the intermediate of the formula (8):

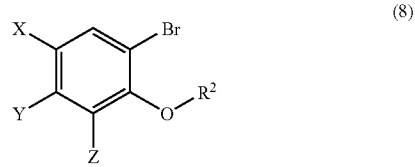

in which R², X, Y and Z are as defined above,
and then by substituting the bromine atom, under the action of an organometallic agent of the formula (9):

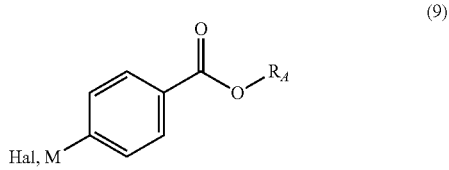

in which Hal represents a halogen atom, for example chlorine, bromine or iodine, preferably iodine, M represents a metal, preferably zinc, and $R_A$ is as defined above and represents, for example, an ethyl radical,
in order to give, under the operating conditions described by E. Negishi et al., *J. Org. Chem.*, 42, (1977), 1821), for example in a polar solvent, preferably dimethylformamide, in the presence of a catalyst, for instance bis(triphenylphosphine)palladium (II) chloride, the compound of the formula (7) defined above, and then the acids of the formula ($1_{OH}$), and optionally the corresponding esters and amides, as defined above.

The compounds of the formula (1) in which R¹ represents —OH can advantageously be obtained by saponification of the corresponding compounds of the formula (1) in which R¹ represents an alkoxy radical, or alternatively starting with the compounds of the formula (7), in which R represents an alkyl radical. The saponification can be performed via the action of a base, such as a mineral base chosen from lithium hydroxide, potassium hydroxide, sodium hydroxide, sodium hydrogen carbonate, potassium hydrogen carbonate, sodium carbonate and potassium carbonate. The molar amount of base to be used generally ranges from 1 to 20 equivalents and preferably from 1 to 12 equivalents depending on the strength of the selected base.

The reaction is preferably performed in a solvent of polar protic type and more preferably in a mixture of a lower ($C_1$-$C_4$) alkanol and water, such as a mixture of ethanol and water or methanol and water.

The reaction temperature advantageously ranges between 35° and 120° C. and better still between 40° and 100° C., for example between 50° C. and reflux.

In the processes described above, it should be understood that the operating conditions may vary substantially as a function of the various substituents present in the compounds of the formula (1) that it is desired to prepare. Such variations and adaptations are readily accessible to those skilled in the art, for example from scientific reviews, the patent literature, Chemical Abstracts, and computer databases, including the Internet. Similarly, the starting materials are either commercially available or accessible via syntheses that a person skilled in the art can readily find, for example in the various publications and databases described above.

The optical isomers of the compounds of the formula (1) can be obtained on the one hand via standard techniques for separating and/or purifying isomers known to those skilled in the art, starting with the racemic mixture of the compound of the formula (1). The optical isomers can also be obtained directly via stereoselective synthesis of an optically active starting compound, or via separation or recrystallisation of the optically active salts of the compounds of the formula (1), the salts being obtained with chiral amines or chiral acids.

Similarly, the possible pharmaceutically acceptable addition salts with acids or bases, and also the possible oxide forms, in particular the N-oxides, are readily accessible from the compounds of the formula (1) according to the operating techniques usually used in this field.

The examples that follow illustrate the present invention without limiting it in any way. In these examples and the proton nuclear magnetic resonance data (300 MHz NMR), the following abbreviations have been used: s for singlet, d for doublet, t for triplet, q for quartet, o for octet and m for complex multiplet. The chemical shifts δ are expressed in ppm.

EXAMPLES

Example 1

Methyl 4-{6-[2-(4-chlorophenyl)thiazol-4-yl-methoxy]-1-oxoindan-5-yl}benzoate

Step 1
A mixture of bis(tricyclohexylphosphine)palladium(II) chloride and hydrazinium hydroxide (0.194 ml; 4 mmol) is stirred for 5 minutes. The reaction is highly exothermic and the yellow medium turns black. The medium is then added to a solution of $Na_3PO_4 \cdot 10H_2O$ (22.8 g; 58.78 mmol) in water (37 ml). The resulting mixture is then stirred for 5 minutes at room temperature, followed by addition of 5-bromo-6-methoxyindan-1-one (9.64 g; 40 mmol), 4-carboxyphenylboronic acid (6.64 g; 40 mmol) and tetrahydrofuran (THF) (74 ml). The reaction medium is refluxed with stirring for 19 hours. It is cooled, acidified with 1N hydrochloric acid and then extracted with ethyl acetate (8.0 g; 71% yield).
¹H NMR (300 MHz, DMSO-D6) δ ppm: 2.7 (dd, J=6.5, 4.8 Hz, 2 H) 3.1 (m, 2 H) 3.8 (s, 3 H) 7.3 (s, 1 H) 7.5 (s, 1 H) 7.6 (m, 2 H) 8.0 (m, 2 H) 12.9 (s, 1 H).

Step 2
A mixture of the compound obtained in step 1 (200 mg; 0.708 mmol) and aluminium trichloride (0.233 g; 1.75 mmol) in toluene (4 ml) is refluxed with stirring for 15 minutes. The brown solution obtained is cooled to room temperature and then poured onto ice. An insoluble material is filtered off (110 mg) and the medium is then extracted with ethyl acetate. The organic phases are dried over sodium sulfate and concentrated to give an additional 46 mg of product (79% total yield).
¹H NMR (300 MHz, DMSO-D6) δ ppm: 2.6 (m, 2 H) 3.0 (m, 2 H) 7.1 (s, 1 H) 7.5 (s, 1 H) 7.7 (d, J=8.2 Hz, 2 H) 8.0 (d, J=8.2 Hz, 2 H) 10.1 (s, 1 H) 13.0 (s, 1 H).
LC/MS ES–267.3.

Step 3
A mixture of the compound obtained in step 2 (130 mg; 0.48 mmol), methanol (5 ml), THF (1 ml) and concentrated sulfuric acid (13 μl) is stirred at reflux. The medium is poured into water and then extracted with ethyl acetate. The organic phases are dried over sodium sulfate and concentrated to give a brown solid (140 mg). Purification by flash chromatography on silica (1/1 heptane/ethyl acetate) gives a yellow solid (100 mg; 74% yield).

$^1$H NMR (300 MHz, chloroform-D) δ ppm: 2.8 (m, 2 H) 3.1 (m, 2 H) 4.0 (s, 3 H) 5.3 (s, 1 H) 7.3 (s, 1 H) 7.4 (s, 1 H) 7.6 (d, J=7.6 Hz, 2 H) 8.2 (d, J=7.2 Hz, 2 H).

LC/MS ES−281.3.

Step 4

A mixture of the compound obtained in step 3 (100 mg; 0.354 mmol), acetone (5 ml), caesium carbonate (127 mg; 0.39 mmol) and 4-chloromethyl-2-(4-chlorophenyl)thiazole (91 mg; 0.373 mmol) is stirred at 55° C. for 9 hours.

The medium is concentrated to dryness and then taken up in water and extracted with methylene chloride. The brown evaporation residue (0.126 g) is purified by flash chromatography on silica (1/1 heptane/ethyl acetate) to give the expected product (57 mg; 31% yield).

$^1$H NMR (300 MHz, chloroform-D) δ ppm: 2.8 (m, 2 H) 3.1 (m, 2 H) 4.0 (s, 3 H) 5.3 (s, 2 H) 7.1 (s, 1 H) 7.4 (m, 4 H) 7.7 (m, 2 H) 7.9 (m, 2 H) 8.1 (m, 2 H).

LC/MS ES+490.1 492.1.

Example 2

4-{6-[2-(4-Chlorophenyl)thiazol-4-ylmethoxy]-1-oxoindan-5-yl}-benzoic acid

A mixture of the compound of Example 1 (57 mg; 0.116 mmol), methanol (2.5 ml), THF (5 ml), aqueous 1N sodium hydroxide (0.15 ml; 0.15 mmol) and water (1.75 ml) is stirred at reflux for 2 hours. The medium is poured into water and then extracted with ether. The mother liquors are acidified with concentrated hydrochloric acid. After extracting with ethyl ether and drying over sodium sulfate, evaporation gives a yellow solid (20 mg) that is purified by flash chromatography on silica (98/2 methylene chloride/methanol) to give the expected product (13 mg; 23% yield).

LC/MS ES−474.3 476.3 ES+476.3 478.2 (one chlorine atom).

Example 3

Ethyl 4-[6-(5-methyl-2-phenyloxazol-4-ylmethoxy)-1-oxoindan-5-yl]benzoate

Step 1

A mixture of 5-bromo-6-hydroxyindan-1-one (3.0 g; 13.2 mmol), acetone (150 ml), caesium carbonate (4.8 g; 14.7 mmol) and 4-chloromethyl-5-methyl-2-phenyloxazole (10.95 g; 52.7 mmol) is stirred at reflux for 6 hours. The medium is poured into water. The precipitate formed is filtered off by suction and then washed with ether (4.67 g; 90% yield).

$^1$H NMR (300 MHz, chloroform-D) δ ppm: 2.5 (s, 3 H) 2.7 (m, 2 H) 3.1 (m, 2 H) 5.1 (s, 2 H) 7.4 (s, 1 H) 7.4 (m, 3 H) 7.7 (s, 1 H) 8.0 (m, 2 H).

Step 2

A mixture of the compound obtained in step 1 (1.2 g; 3.01 mmol) and Pd(PPh$_3$)$_2$Cl$_2$ (90 mg) in dimethylformamide (DMF) (16 ml) is warmed to +33° C., and a 0.5N solution in THF of 4-(ethoxycarbonyl)phenylzinc iodide (7.3 ml; 3.65 mmol) is then added dropwise. The medium is stirred overnight at room temperature and then poured into a mixture of water and ethyl acetate. After filtration through Hyflo, the organic phase is dried over sodium sulfate and concentrated to give a pasty orange solid, which is triturated in ethyl ether. The dispersed precipitate is filtered off by suction (704 mg).

Purification by flash chromatography on silica (20/80 heptane/methylene chloride) gives the expected product (380 mg; 27% yield).

$^1$H NMR (300 MHz, chloroform-D) δ ppm: 1.4 (t, J=7.1 Hz, 3 H) 2.2 (s, 3 H) 2.8 (m, 2 H) 3.1 (m, 2 H) 4.4 (q, J=7.1 Hz, 2 H) 5.0 (s, 2 H) 7.4 (m, 4 H) 7.5 (s, 1 H) 7.6 (m, 2 H) 8.0 (m, 2 H) 8.0 (m, 2 H).

Example 4

4-[6-(5-Methyl-2-phenyloxazol-4-ylmethoxy)-1-oxoindan-5-yl]-benzoic acid

A mixture of the compound obtained in Example 3 (1.7 g; 3.64 mmol), methanol (42 ml), THF (85 ml), aqueous 1N sodium hydroxide (3.4 ml; 3.4 mmol) and water (42 ml) is stirred at reflux for 1.25 hours. The medium is cooled and poured into water and then acidified with concentrated hydrochloric acid. After extracting with methylene chloride and drying over sodium sulfate, evaporation gives a beige-coloured solid (1.56 g). Flash chromatography on silica (95/5 methylene chloride/methanol) gives the expected product (954 mg; 60% yield).

$^1$H NMR (300 MHz, DMSO-D6) δ ppm: 2.4 (s, 3 H) 2.7 (m, 2 H) 3.1 (m, 2 H) 5.1 (s, 2 H) 7.5 (m, 8 H) 7.9 (m, 4 H)

LC/MS ES+440.1.

Example 5

Ethyl 5'-fluoro-2'-[2-(5-methyl-2-phenyloxazol-4-yl)ethoxy]-biphenylcarboxylate

Step 1

To a mixture, preheated to 54° C., of 2-bromo-4-fluorophenol (0.5 g; 2.61 mmol), triphenylphosphine (0.752 g; 2.87 mmol) and 2-(5-methyl-2-phenyloxazol-4-yl)ethanol (0.858 g; 2.87 mmol) in toluene (10 ml) is added dropwise a solution of diisopropyl azodicarboxylate (0.504 ml; 2.54 mmol) in toluene (10 ml). The reaction medium, which turns red, is stirred for a further 1 hour at 54° C. The solvent is concentrated to dryness and the evaporation residue is purified by flash chromatography on silica (85/15 heptane/ethyl acetate). 0.8 g of the expected product is obtained (81% yield).

$^1$H NMR (300 MHz, chloroform-D) δ ppm: 2.4 (s, 3 H) 3.0 (t, J=6.4 Hz, 2 H) 4.3 (t, J=6.4 Hz, 2 H) 6.9 (m, 2 H) 7.3 (m, 1 H) 7.4 (m, 3 H) 8.0 (m, 2 H).

Step 2

A 0.5N solution in THF of 4-(ethoxycarbonyl)phenylzinc iodide (14 ml; 7 mmol) is added dropwise to a mixture of the compound obtained in step 1 (0.8 g; 2.126 mmol) and Pd(PPh$_3$)$_2$Cl$_2$ (142 mg) in DMF (34 ml). The temperature rises to 27° C. The medium is refluxed for 3 hours and then poured into water. The medium is extracted with ethyl ether and ethyl acetate. The organic phases are dried over sodium sulfate and concentrated to give a brown oil (1.7 g). Purification by flash chromatography on silica (90/10 heptane/ethyl acetate) gives the expected product (0.128 mg; 14% yield).

LC/MS ES+446.4.

Example 6

5'-Fluoro-2'-[2-(5-methyl-2-phenyloxazol-4-yl)ethoxy]biphenyl-carboxylic acid

A mixture of the compound obtained in Example 5 (0.128 g; 0.287 mmol), methanol (2.5 ml), THF (5 ml), aqueous 1N sodium hydroxide (0.37 ml; 0.37 mmol) and water (2.5 ml) is stirred at reflux for 1 hour. The medium is then cooled and poured into water. After extracting with ethyl ether, the aqueous phase is acidified with concentrated hydrochloric acid.

The white precipitate formed is taken up in ethyl acetate. Evaporation gives a beige-coloured solid (76 mg; 63% yield).
¹H NMR (300 MHz, DMSO-D6) δ ppm: 2.1 (s, 3 H) 2.9 (t, J=6.0 Hz, 2 H) 4.3 (t, J=6.0 Hz, 2 H) 7.2 (m, 3 H) 7.5 (m, 5 H) 7.9 (m, 4 H) 13.0 (s, 1 H).
LC/MS ES+418.3.

Compounds 7 to 48 were prepared according to protocols similar to those described for the preparation of the compounds of Examples 1 to 6 above.

The structures of compounds 7 to 48 are collated in Table 1 below:

TABLE 1

Structures of compounds 7 to 48

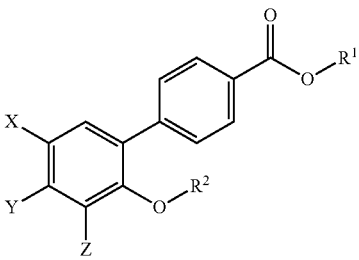

| Ex. | R¹ | R² | X | Y | Z |
|---|---|---|---|---|---|
| 7 | —CH₂—CH₃ | 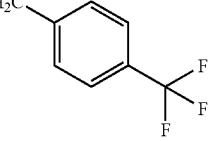 | 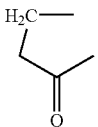 | | —H |
| 8 | —CH₂—CH₃ |  | 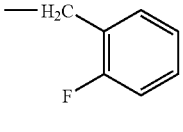 | | —H |
| 9 | —H | 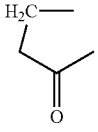 |  | | —H |
| 10 | —H | 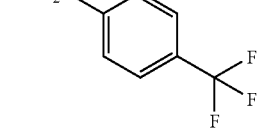 | 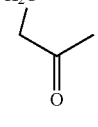 | | —H |
| 11 | —CH₂—CH₃ |  | 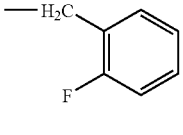 | | —H |
| 12 | —H | 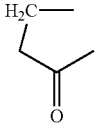 |  | | —H |

TABLE 1-continued
Structures of compounds 7 to 48
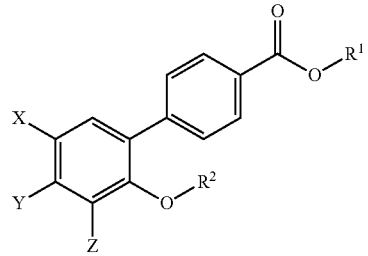
| Ex. | R¹ | R² | X | Y | Z |
|---|---|---|---|---|---|
| 13 | —CH₂—CH₃ | 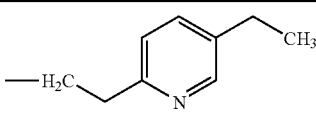 | 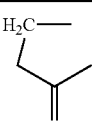 | | —H |
| 14 | —H | 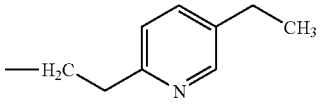 | 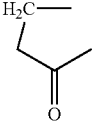 | | —H |
| 15 | —CH₂—CH₃ | —(CH₂)₄—CH₃ | 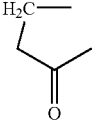 | | —H |
| 16 | —H | —(CH₂)₃—CH₃ | 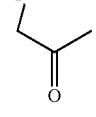 | | —H |
| 17 | —CH₂—CH₃ | —(CH₂)₅—CH₃ | 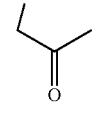 | | —H |
| 18 | —H | —(CH₂)₄—CH₃ | 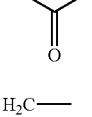 | | —H |
| 19 | —H | —(CH₂)₅—CH₃ | 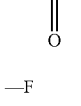 | | —H |
| 20 | —CH₂—CH₃ | 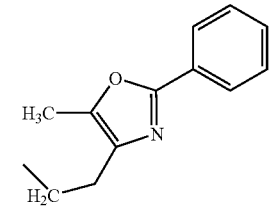 | —F | —H | —H |

TABLE 1-continued
Structures of compounds 7 to 48
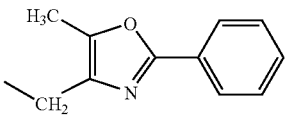
| Ex. | R¹ | R² | X | Y | Z |
|---|---|---|---|---|---|
| 21 | —H | 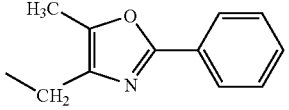 | —F | —H | —H |
| 22 | —CH₂—CH₃ | 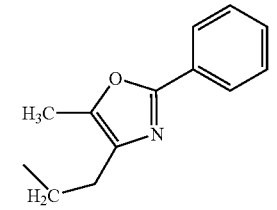 | —O—CH₃ | —H | —H |
| 23 | —H | 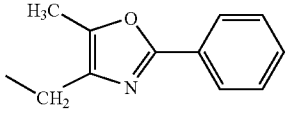 | —O—CH₃ | —H | —H |
| 24 | —H | 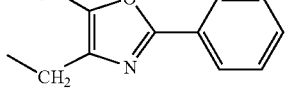 | —O—CH₃ | —H | —H |
| 25 | —CH₂—CH₃ | 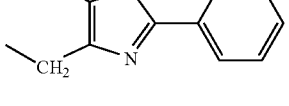 | —CH₃ | —H | —H |
| 26 | —H | 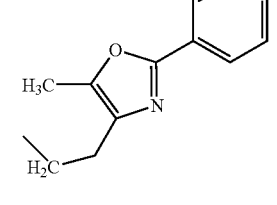 | —CH₃ | —H | —H |
| 27 | —H | 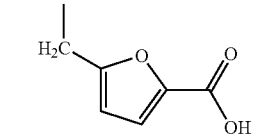 | —CH₃ | —H | —H |
| 28 | —H | 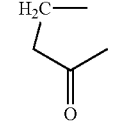 | | | —H |

TABLE 1-continued

Structures of compounds 7 to 48

| Ex. | R¹ | R² | X | Y | Z |
|---|---|---|---|---|---|
| 29 | —H | 3-(CH₂-)-5-methylisoxazole | -CH₂-C(=O)-CH₃ | | —H |
| 30 | —H | 4-(CH₂-)-5-methyl-2-phenyl-2H-1,2,3-triazole | -CH₂-C(=O)-CH₃ | | —H |
| 31 | —H | 4-(CH₂-)-2-(thiophen-2-yl)thiazole | -CH₂-C(=O)-CH₃ | | —H |
| 32 | —H | 4-(CH₂-)-5-methyl-3-phenylisoxazole | -CH₂-C(=O)-CH₃ | | —H |
| 33 | —H | 3-(CH₂-)-1-(pyrrol-1-yl)phenyl | -CH₂-C(=O)-CH₃ | | —H |
| 34 | —H | 3-(CH₂-)-5-tert-butyl-1,2,4-oxadiazole | -CH₂-C(=O)-CH₃ | | —H |

TABLE 1-continued

Structures of compounds 7 to 48

| Ex. | R¹ | R² | X | Y | Z |
|---|---|---|---|---|---|
| 35 | —H | 1-(3-phenyl-1,2,4-oxadiazol-5-yl)ethyl (via CH₂) | H₃C-C(=O)-CH₂— | | —H |
| 36 | —H | 1-(3-carboxyfuran-2-yl)ethyl | H₃C-C(=O)-CH₂— | | —H |
| 37 | —H | 1-(5-(thiophen-2-yl)-1,2,4-oxadiazol-3-yl)ethyl | H₃C-C(=O)-CH₂— | | —H |
| 38 | —H | 1-(4-(1H-pyrrol-1-yl)phenyl)ethyl | H₃C-C(=O)-CH₂— | | —H |
| 39 | —H | 1-(5-methyl-2-phenyloxazol-4-yl)ethyl | —Cl | —H | —H |
| 40 | —H | 1-(5-(trifluoromethyl)furan-2-yl)ethyl | H₃C-C(=O)-CH₂— | | —H |
| 41 | —H | 1-(5-(4-methoxyphenyl)-1,2,4-oxadiazol-3-yl)ethyl | H₃C-C(=O)-CH₂— | | —H |
| 42 | —CH₂—CH₃ | 1-(5-methyl-2-phenyloxazol-4-yl)ethyl | —F | —H | —F |

TABLE 1-continued
Structures of compounds 7 to 48
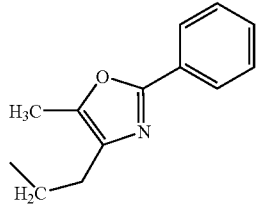
| Ex. | R¹ | R² | X | Y | Z |
|---|---|---|---|---|---|
| 43 | —H | 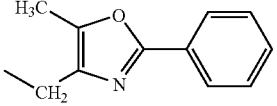 | —Cl | —H | —H |
| 44 | —H | 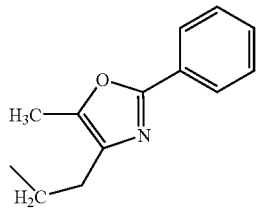 | —F | —H | —F |
| 45 | —CH₂—CH₃ | 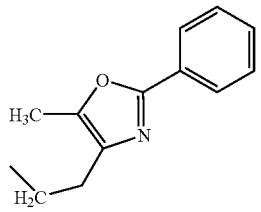 | —F | —H | —F |
| 46 | —H | 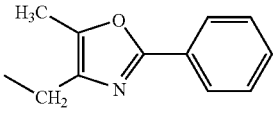 | —F | —H | —F |
| 47 | —H | 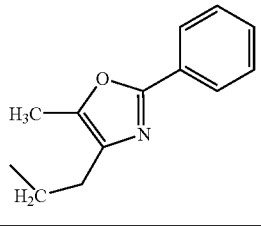 | —F | —F | —H |
| 48 | —H |  | —F | —F | —H |

The results of the analyses of the synthesised products 7 to 48 are given in Table 2 below, in which table:

M represents the theoretical molar mass of the compound;

NMR indicates the chemical shifts δ (in ppm) of the proton by magnetic resonance at 300 MHz; and LC/MS indicates the result of the analysis by mass spectrometry coupled to liquid-phase chromatography.

TABLE 2

| Ex. | M | NMR | LC/MS |
|---|---|---|---|
| 7 | 454.44 | $^1$H NMR (300 MHz, chloroform-D) δ ppm 1.4 (t, J = 7.2 Hz, 3 H) 2.8 (m, 2 H) 3.1 (m, 2 H) 4.4 (q, J = 7.1 Hz, 2 H) 5.2 (s, 2 H) 7.4 (m, 3 H) 7.5 (s, 1 H) 7.6 (m, 4 H) 8.1 (m, 2 H) | ES+ 455.3 ES− 453.3 |
| 8 | 404.44 | $^1$H NMR (300 MHz, chloroform-D) δ ppm 1.4 (t, J = 7.2 Hz, 3 H) 2.8 (dd, J = 6.7, 4.8 Hz, 2 H) 3.1 (m, 2 H) 4.4 (q, J = 7.1 Hz, 2 H) 5.2 (s, 2 H) 7.1 (m, 2 H) 7.3 (m, 2 H) 7.4 (s, 1 H) 7.5 (s, 1 H) 7.6 (m, 2 H) 8.1 (m, 2 H) | ES+ 405.3 |
| 9 | 426.39 | $^1$H NMR (300 MHz, DMSO-D6) δ ppm 2.7 (m, 2 H) 3.1 (m, 2 H) 5.3 (s, 2 H) 7.4 (s, 1 H) 7.6 (m, 3 H) 7.7 (m, 4 H) 8.0 (dd, J = 8.3, 1.6 Hz, 2 H) 13.0 (s, 1 H) | ES+ 427.3 ES− 425.3 |
| 10 | 376.38 | $^1$H NMR (300 MHz, DMSO-D6) δ ppm 2.7 (s, 2 H) 3.1 (m, 2 H) 5.3 (s, 2 H) 7.2 (m, 2 H) 7.4 (m, 3 H) 7.6 (s, 1 H) 7.7 (m, J = 7.8 Hz, 2 H) 7.9 (m, 2 H) 13.0 (s, 1 H) | ES+ 377.3 ES− 375.3 |
| 11 | 481.55 | $^1$H NMR(300 MHz, chloroform-D) δ ppm 1.4 (t, J = 7.1 Hz, 3 H) 2.1 (s, 3 H) 2.7 (dd, J = 6.6, 4.9 Hz, 2 H) 2.9 (t, J = 6.2 Hz, 2 H) 3.1 (m, 2 H) 4.3 (t, J = 6.2 Hz, 2 H) 4.4 (q, J = 7.1 Hz, 2 H) 7.4 (m, 7 H) 8.0 (m, 4 H) | ES+ 482.4 |
| 12 | 453.49 | $^1$H NMR (300 MHz, DMSO-D6) δ ppm 2.1 (s, 3 H) 2.7 (m, 2 H) 2.9 (m, 2 H) 3.1 (m, 2 H) 4.3 (t, J = 6.1 Hz, 2 H) 7.3 (s, 1 H) 7.5 (m, 6 H) 7.9 (m, 4 H) 13.0 (s, 1 H) | ES+ 454.4 ES− 452.5 |
| 13 | 429.51 | $^1$H NMR (300 MHz, chloroform-D) δ ppm 1.3 (t, J = 7.6 Hz, 3 H) 1.4 (t, J = 7.2 Hz, 3 H) 2.7 (m, 4 H) 3.1 (m, 4 H) 4.4 (m, 4 H) 6.9 (d, J = 7.8 Hz, 1 H) 7.3 (m, 5 H) 8.0 (d, J = 8.2 Hz, 2 H) 8.4 (s, 1 H) | ES+ 430.4 |
| 14 | 401.46 | | ES+ 402.4 ES− 400.4 |
| 15 | 366.45 | $^1$H NMR (300 MHz, chloroform-D) δ ppm 0.9 (t, J = 6.9 Hz, 3 H) 1.3 (m, 4 H) 1.4 (t, J = 7.2 Hz, 3 H) 1.7 (m, 2 H) 2.7 (m, 2 H) 3.1 (m, 2 H) 4.0 (t, J = 6.6 Hz, 2 H) 4.4 (q, J = 7.1 Hz, 2 H) 7.3 (s, 1 H) 7.4 (s, 1 H) 7.6 (m, 2H) 8.1 (m, 2 H) | ES+ 367.3 |
| 16 | 324.37 | | ES+ 325.3 ES− 323.3 |
| 17 | 380.48 | $^1$H NMR (300 MHz, chloroform-D) δ ppm 0.9 (t, J = 6.8 Hz, 3 H) 1.3 (m, 6 H) 1.4 (t, J = 7.2 Hz, 3 H) 1.7 (m, 2 H) 2.8 (m, 2 H) 3.1 (m, 2 H) 4.0 (t, J = 6.5 Hz, 2 H) 4.4 (q, J = 7.1 Hz, 2 H) 7.3 (s, 1 H) 7.4 (s, 1 H) 7.6 (d, J = 8.2 Hz, 2 H) 8.1 (d, J = 8.2 Hz, 2 H) | ES+ 381.3 |
| 18 | 338.40 | $^1$H NMR (300 MHz, chloroform-D) δ ppm 0.9 (t, J = 7 Hz, 3 H) 1.3 (m, 4 H) 1.7 (m, 2 H) 2.8 (m, 2 H) 3.1 (m, 2 H) 4.0 (t, J = 6.5 Hz, 2 H) 7.3 (s, 1 H) 7.4 (s, 1 H) 7.7 (m, 2 H) 8.2 (m, 2 H) | ES+ 33 + 9.3 ES− 337.3 |
| 19 | 352.43 | $^1$H NMR (300 MHz, DMSO-D6) δ ppm 0.8 (t, J = 7 Hz, 3 H) 1.2 (m, 6 H) 1.6 (m, 2 H) 2.7 (m, 2 H) 3.1 (m, 2 H) 4.0 (t, J = 6.2 Hz, 2 H) 7.2 (s, 1 H) 7.5 (s, 1 H) 7.6 (d, J = 8.4 Hz, 2 H) 8.0 (d, J = 8.4 Hz, 2 H) 13.0 (s, 1 H) | ES+ 353.4 ES− 351.4 |
| 20 | 445.49 | | ES+ 446.4 |
| 21 | 403.41 | | ES+ 404.3 ES− 402.3 |
| 22 | 443.50 | $^1$H NMR (300 MHz, chloroform-D) δ ppm 1.5 (t, J = 7.2 Hz, 3 H) 2.2 (s, 3 H) 4.0 (s, 3 H) 4.5 (q, J = 7.2 Hz, 2 H) 5.0 (s, 2 H) 7.0 (dd, J = 7.2, 2.7 Hz, 1 H) 7.3 (m, 1 H) 7.6 (m, 3 H) 7.8 (m, 2 H) 8.1 (m, 2 H) 8.2 (m, 2 H) | ES+ 444.3 |
| 23 | 429.47 | $^1$H NMR (300 MHz, DMSO-D6) δ ppm 2.1 (s, 3 H) 2.8 (t, J = 6.0 Hz, 2 H) 3.7 (s, 3 H) 4.2 (t, J = 6.0 Hz, 2 H) 6.9 (m, 2 H) 7.1 (m, 1 H) 7.5 (m, 5 H) 7.9 (m, 4 H) 12.9 (s, 1 H) | ES+ 430.3 ES− 428.4 |

TABLE 2-continued

| Ex. | M | NMR | LC/MS |
|---|---|---|---|
| 24 | 415.44 | 1H NMR (300 MHz, DMSO-D6) δ ppm 2.3 (s, 3 H) 3.8 (s, 3 H) 4.9 (s, 2 H) 6.9 (m, 2 H) 7.3 (d, J = 9.0 Hz, 1 H) 7.5 (dd, J = 5.0, 1.7 Hz, 3 H) 7.7 (m, 2 H) 7.9 (m, 4 H) 12.9 (s, 1 H) | ES+ 416.3 ES− 414.4 |
| 25 | 427.50 | 1H NMR (300 MHz, chloroform-D) δ ppm 1.4 (m, 3 H) 2.1 (s, 3 H) 2.3 (s, 3 H) 4.4 (q, J = 7.2 Hz, 2 H) 4.9 (s, 2 H) 7.1 (m, 3 H) 7.4 (m, 3 H) 7.6 (d, J = 8.6 Hz, 2 H) 8.0 (m, 4 H) | ES+ 428.3 |
| 26 | 399.44 | 1H NMR (300 MHz, DMSO-D6) δ ppm 2.3 (s, 3 H) 2.3 (s, 3 H) 5.0 (s, 2 H) 7.2 (m, J = 13.5 Hz, 3 H) 7.5 (m, 3 H) 7.6 (d, J = 8.2 Hz, 2H) 7.9 (m, 4 H) 12.9 (s, 1 H) | ES+ 400.3 ES− 398.4 |
| 27 | 413.47 | | ES+ 414.3 ES− 412.4 |
| 28 | 392.36 | | ES+ 415.2 (M + Na) 393.2 375.2 ES− 391.3 |
| 29 | 363.37 | | ES+ 364.2 ES− 362.3 |
| 30 | 439.47 | | ES+ 440.3 ES− 438.4 |
| 31 | 447.53 | | ES+ 448.2 ES− 446.3 |
| 32 | 439.47 | | ES+ 440.3 ES− 438.3 |
| 33 | 423.47 | | ES+ 424. ES− 422.3 |
| 34 | 406.44 | | ES+ 407.3 ES− 405.3 |
| 35 | 426.43 | | ES+ 427.2 ES− 425.3 |
| 36 | 392.36 | | ES+ 415.2 393.2 375.2 ES− 391.3 |
| 37 | 432.45 | | ES+ 433.2 ES− 431.3 |
| 38 | 423.47 | | ES+ 424.3 ES− 422.3 |
| 39 | 419.86 | 1H NMR (300 MHz, DMSO-D6) δ ppm 2.3 (s, 3 H) 5.1 (s, 2 H) 7.5 (m, 6 H) 7.7 (d, J = 8.2 Hz, 2 H) 7.9 (m, 4 H) 12.9 (s, 1 H) | ES+ 420.1 422.1 ES− 420.2 418.2 1 atome de chlore |
| 40 | 416.35 | | ES+ 417.2 ES− 415.2 |
| 41 | 456.45 | | ES+ 457.3 ES− 455.3 |
| 42 | 449.45 | 1H NMR (300 MHz, chloroform-D) δ ppm 1.4 (t, J = 7.2 Hz, 3 H) 2.0 (s, 3 H) 4.3 (q, J = 7.2 Hz, 2 H) 4.8 (s, 2 H) 6.9 (m, 2 H) 7.4 (m, 3 H) 7.5 (d, J = 8.2 Hz, 2 H) 7.8 (m, 2 H) 7.9 (d, J = 8.2 Hz, 2 H) | ES+ 450.2 |
| 43 | 433.89 | | ES+ 434.2 436.2 ES− 432.3 434.3 1 atome de chlore |
| 44 | 421.40 | 1H NMR (300 MHz, chloroform-D) δ ppm 2.0 (s, 3 H) 4.8 (s, 2 H) 6.9 (m, 2 H) 7.4 (m, 3 H) 7.5 (d, J = 8.4 Hz, 2 H) 7.8 (m, 2 H) 8.0 (d, J = 8.2 Hz, 2 H) | ES+ 422.1 ES− 420.2 |
| 45 | 463.48 | 1H NMR (300 MHz, chloroform-D) δ ppm 1.4 (t, J = 7.1 Hz, 3 H) 2.2 (s, 3 H) 2.7 (t, J = 6.5 Hz, 2 H) 4.1 (t, J = 6.5 Hz, 2 H) 4.3 (q, J = 7.1 Hz, 2 H) 6.8 (m, 2 H) 7.4 (m, 3 H) 7.5 (m, 2 H) 7.9 (m, 2 H) 7.9 (m, 2 H) | ES+ 464.3 |
| 46 | 435.42 | 1H NMR (300 MHz, chloroform-D) δ ppm 2.2 (s, 3 H) 2.8 (t, J = 6.3 Hz, 2 H) 4.1 (m, 2 H) 6.9 (m, 2 H) 7.4 (m, 3 H) 7.5 (d, J = 8.4 Hz, 2 H) 7.9 (m, 2 H) 8.0 (m, 2 H) | ES+ 436.3 ES− 434.3 |
| 47 | 421.40 | | ES+ 422.2 ES− 420.3 |
| 48 | 435.42 | 1H NMR (300 MHz, DMSO-D6) δ ppm 2.1 (s, 3 H) 2.9 (t, J = 5.9 Hz, 2 H) 4.3 (t, J = 5.9 Hz, 2 H) 7.4 (m, 7 H) 7.9 (m, 4 H) 13.0 (s, 1 H) | ES+ 436.3 ES− 434.3 |

RESULTS

The measurement of the PPAR activation was performed according to a technique described by Lehmann et al. (*J. Biol. Chem.*, 270, (1995), 12953-12956).

CV-1 cells (monkey kidney cells) are cotransfected with an expression vector for the chimeric protein PPARγ-Gal4 and with a "reporter" plasmid that allows expression of the luciferase gene placed under the control of a promoter comprising Gal4 response elements.

The cells are seeded in 96-well microplates and cotransfected using a commercial reagent with the reporter plasmid (pG5-tk-pGL3) and the expression vector for the chimeric protein (PPARγ-Gal4). After incubation for 4 hours, whole culture medium (comprising 10% foetal calf serum) is added to the wells. After 24 hours, the medium is removed and replaced with whole medium comprising the test products. The products are left in contact with the cells for 18 hours. The cells are then lysed and the luciferase activity is measured using a luminometer. A PPARγ activation factor can then be calculated by means of the activation of the expression of the reporter gene induced by the product (relative to the control cells that have received no product).

In the absence of the PPARγ ligand binding domain (vector expressing Gal4 alone), the luciferase activity measured in the presence of this product is zero.

The following transactivation result was obtained with a concentration of 30 μM on PPARγ.

| Ex. | Concentration | Activation factor of the chimeric protein PPARγ-Gal4 |
|---|---|---|
| 29 | 30 μM | 16 |
| Without agonist (Control) | — | 1 |

Example of Biological Activities of Partial Agonists

Transactivation Test

The transactivation test using the expression of a chimeric protein Gal-4-PPARγ makes it possible to determine also whether an agonist functions as a "full" agonist or as a "partial" agonist in this system.

An agonist is "partial" in this system if it induces a weaker response, i.e. it has lower efficacy, than rosiglitazone, which is a "full" agonist. In concrete terms, in our system, the transactivation obtained at the plateau with a partial agonist will be between 20% and 50% of the maximum response (efficacy) at the plateau of rosiglitazone.

| Ex. | Maximum stimulation of the PPARγ chimeric protein obtained with rosiglitazone | Concentration to reach the maximum stimulation of the PPARγ chimeric protein |
|---|---|---|
| 4 | 23% | 6.25 μM |

The invention claimed is:

1. A compound of formula (1):

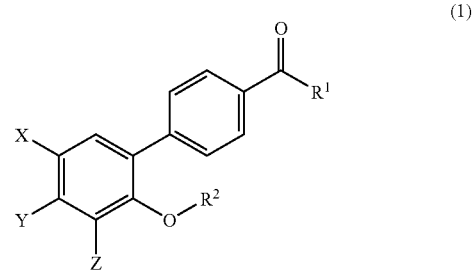

in which:
$R^1$ represents —O—$R'^1$ or —$NR'^1R''^1$, with
$R'^1$ and $R''^1$ are, each independently, a hydrogen atom, an alkyl radical, an alkenyl radical, an alkynyl radical, a cycloalkyl radical, an aryl radical or a heteroaryl radical;
$R^2$ is a propyl, isopropyl, butyl, isobutyl, tert-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 1-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyloctyl or 7,7-dimethyloctyl group, or an alkenyl or alkynyl radical, or an optionally substituted arylalkyl radical, or an optionally substituted heterocyclylalkyl radical;
X and Y are, each independently, a hydrogen atom, a halogen atom, an alkyl radical or an alkoxy radical;
or alternatively
X and Y together form, with the carbon atoms that bear them, a 5-membered ring containing a ketone function; and
Z is a hydrogen atom, a halogen atom, or an alkyl radical;
or an optical isomer, oxide form, or a pharmaceutically acceptable addition salt thereof with an acid or base.

2. A compound according to claim 1, having one or more of the following characteristics, taken separately or as a combination of one, several or all of them:
$R^1$ represents —O—$R'^1$, wherein $R'^1$ is a hydrogen atom, an alkyl radical, an alkenyl radical, an alkynyl radical, a cycloalkyl radical, an aryl radical and a heteroaryl radical;
$R^2$ is propyl, isopropyl, butyl, isobutyl, tert-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 1-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyloctyl or 7,7-dimethyloctyl group, or an optionally substituted benzyl radical or an optionally substituted heterocyclylalkyl radical;
X and Y, which may be identical or different, are, independently of each other, a hydrogen atom, a halogen atom, an alkyl radical or an alkoxy radical; or alternatively X and Y together form, with the carbon atoms that bear them, a 5-membered ring containing a ketone function; or
Z is a hydrogen atom, a halogen atom, or an alkyl radical.

3. A compound according to claim 1, having one or more of the following characteristics, taken separately or as a combination of one, several or all of them:
- $R^1$ represents —O—$R'^1$, wherein $R'^1$ is a hydrogen atom or an alkyl radical;
- $R^2$ is propyl, isopropyl, butyl, isobutyl, tert-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 1-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyloctyl or 7,7-dimethyloctyl group, or an optionally substituted benzyl radical or an optionally substituted heterocyclylalkyl radical;
- X and Y, which may be identical or different, are, independently of each other, a hydrogen atom, a halogen atom, an alkyl radical and an alkoxy radical; or alternatively X and Y together form, with the carbon atoms that bear them, a 5-membered ring containing a ketone function; or
- Z is a hydrogen atom or a halogen atom.

4. A compound according to claim 1, having one or more of the following characteristics, taken separately or as a combination of one, several or all of them:
- $R^1$ represents —O—$R'^1$, wherein $R'^1$ is a hydrogen atom, a methyl radical or an ethyl radical;
- $R^2$ is propyl, isopropyl, butyl, isobutyl, tert-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 1-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyloctyl or 7,7-dimethyloctyl group, or an optionally substituted benzyl radical or an optionally substituted heterocyclylalkyl radical;
- X and Y, which may be identical or different, are, independently of each other, a hydrogen atom, a fluorine atom, a chlorine atom, a methyl radical or a methoxy radical; or alternatively X and Y together form, with the carbon atoms that bear them, a cyclopentenone ring; or
- Z is a hydrogen atom, a fluorine atom or a chlorine atom.

5. A compound according to claim 1, wherein the substituents of the radicals of the compounds of the formula (1) are a halogen atom, or a methyl, ethyl, methoxy, phenyl, trifluoromethyl or a trifluoromethoxy group.

6. A compound according to claim 1, wherein the heterocyclic radicals are selected from the group consisting of furyl, thienyl, pyrrolyl, pyridyl, triazolyl, oxazolidinyl, thiazolyl, oxadiazolyl and oxazolyl radicals.

7. A compound, which is
4-[6-(5-methyl-2-phenyloxazol-4-ylmethoxy)-1-oxoindan-5-yl]benzoic acid;
4-[1-oxo-6-(4-trifluoromethylbenzyloxy)indan-5-yl]benzoic acid;
4-[6-(2-fluorobenzyloxy)-1-oxoindan-5-yl]benzoic acid;
5'-methoxy-2'-(5-methyl-2-phenyloxazol-4-ylmethoxy) biphenyl-4-carboxylic acid;
5'-methyl-2'-(5-methyl-2-phenyloxazol-4-ylmethoxy)biphenyl-4-carboxylic acid;
4-[6-(5-methylisoxazol-3-ylmethoxy)-1-oxoindan-5-yl] benzoic acid;
4-[6-(5-methyl-2-phenyl-2H-[1,2,3]triazol-4-ylmethoxy)-1-oxoindan-5-yl]benzoic acid;
4-[1-oxo-6-(2-thiophen-2-ylthiazol-4-ylmethoxy)indan-5-yl]benzoic acid;
4-[6-(5-methyl-3-phenylisoxazol-4-ylmethoxy)-1-oxoindan-5-yl]benzoic acid;
methyl 4-{6-[2-(4-chlorophenyl)thiazol-4-ylmethoxy]-1-oxoindan-5-yl}benzoate;
4-{6-[2-(4-chlorophenyl)thiazol-4-ylmethoxy]-1-oxoindan-5-yl}benzoic acid;
ethyl 4-[6-(5-methyl-2-phenyloxazol-4-ylmethoxy)-1-oxoindan-5-yl]benzoate;
5'-fluoro-2'-[2-(5-methyl-2-phenyloxazol-4-yl)ethoxy]biphenylcarboxylate;
5'-Fluoro-2'-[2-(5-methyl-2-phenyloxazol-4-yl)ethoxy] biphenylcarboxylic acid; or
one of the following compounds

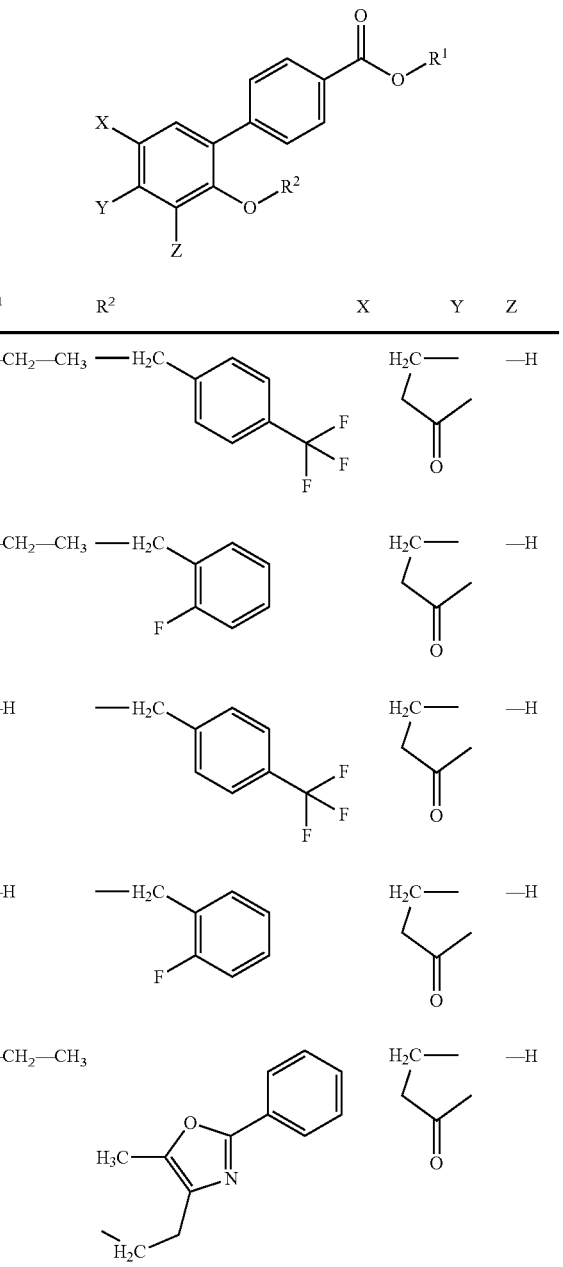

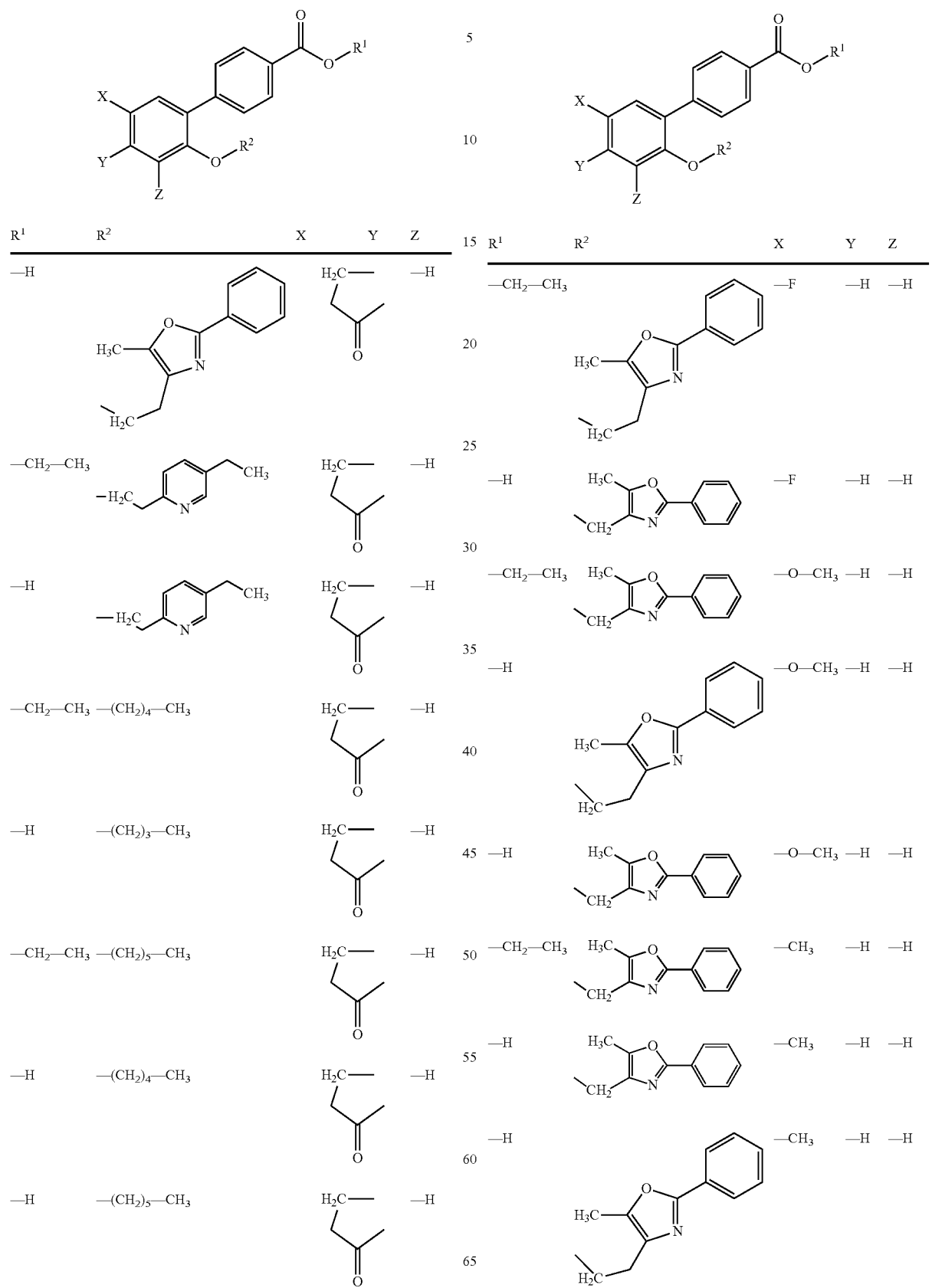

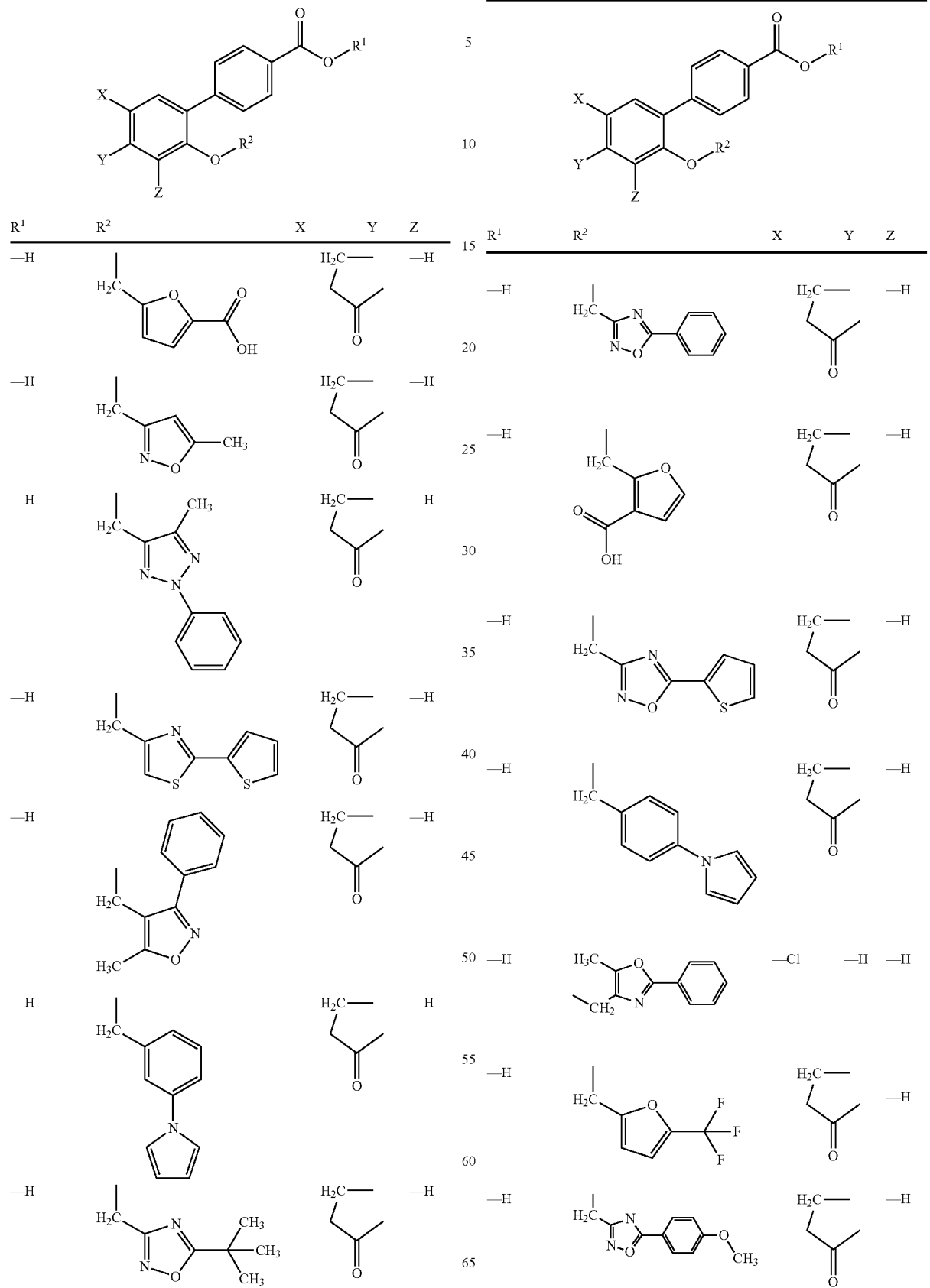

-continued

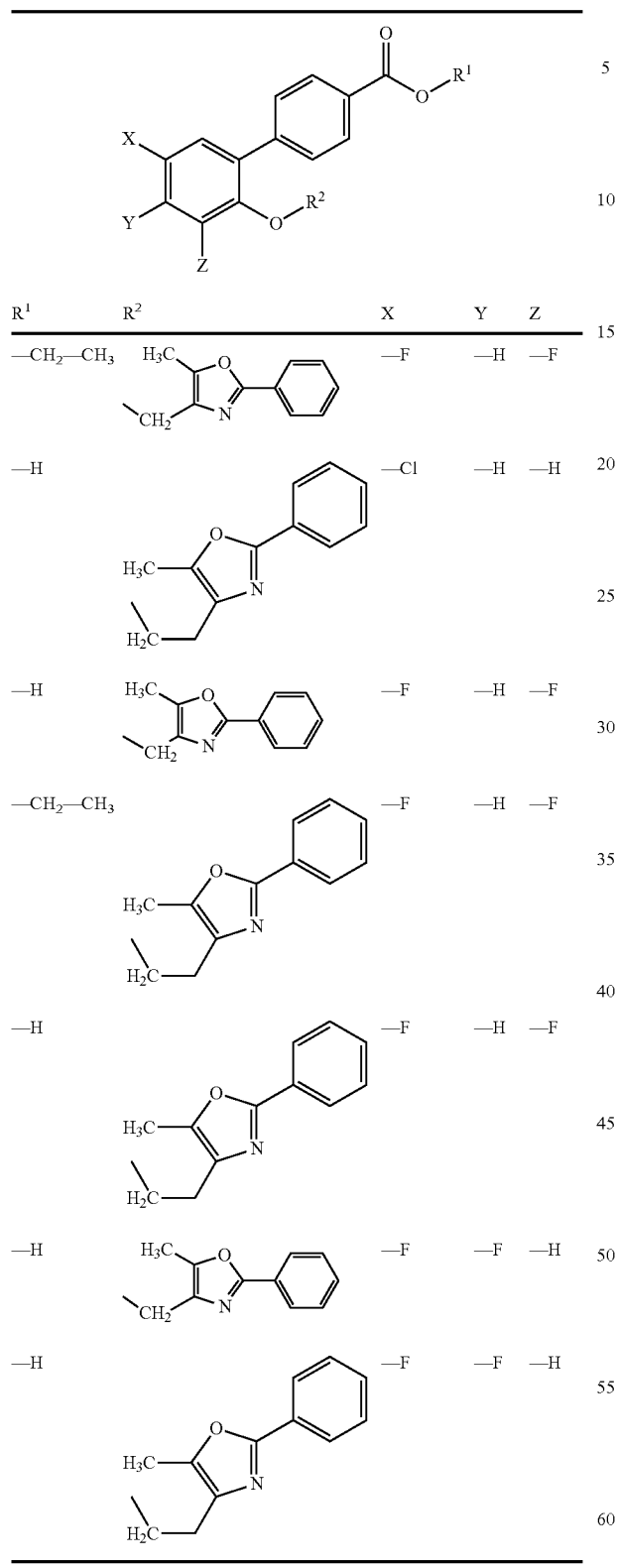

or an optical isomer, oxide form, or a pharmaceutically acceptable addition salt thereof with an acid or base.

8. A process for preparing a compound of claim 1, comprising subjecting a compound of formula (2):

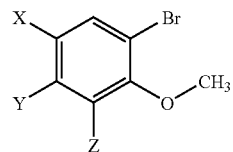
(2)

in which X, Y and Z are as defined for the compound of formula (1), to the action of a boronic acid of formula (3):

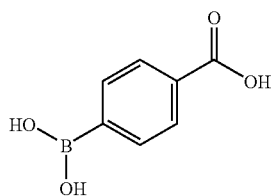
(3)

in the presence of a catalyst, in the presence of hydrazinium hydroxide and trisodium phosphate, in polar protic medium, to give a compound of formula (4):

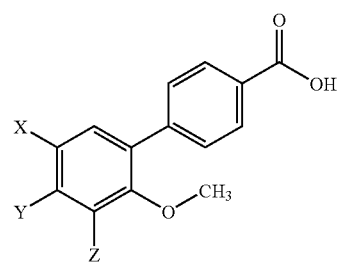
(4)

in which X, Y and Z are as defined for the compound of formula (1), in which compound of formula (4) the methoxy function is converted into an alcohol function to give a compound of formula (5):

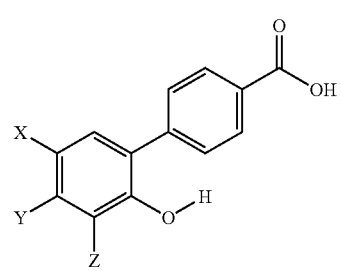
(5)

in which X, Y and Z are as defined for the compound of formula (1), and then esterifying, in order to protect the acid function, with an alcohol $R_4$—OH, in which $R_4$ represents a linear or branched alkyl radical containing from 1 to 4 carbon atoms, in the presence of a strong acid, to give the ester of formula (6):

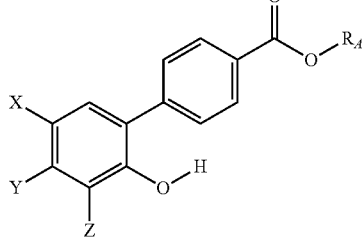

(6)

in which $R_A$ is as defined above, and X, Y and Z are as defined for the compound of formula (1), which compound of the formula (6) is then subjected to the action of a halide of formula Hal-$R^2$, in which Hal represents a halogen atom, and $R^2$ is as defined for the compound of formula (1), in the presence of a base and optionally in the presence of an activator in polar aprotic medium, to give a compound of formula (7):

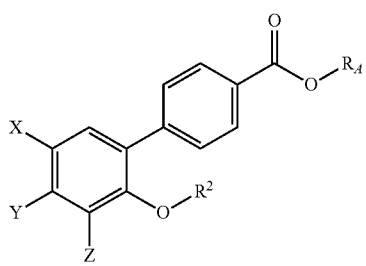

(7)

in which $R^2$, X, Y and Z are as defined for the compound of formula (1), and $R_A$ is as defined above, the protecting group $R_A$ of which is then removed to give an acid of formula ($1_{OH}$):

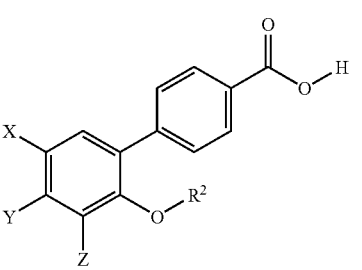

($1_{OH}$)

which is a special case of the compounds of the formula (1) in which $R^1$ represents a hydroxyl radical, and the acid is optionally esterified, or converted into a corresponding amide to give a compound of formula (1), with $R^1$ other than a hydroxyl radical.

9. A process for preparing a compound of claim 1, comprising subjecting a compound of formula (2):

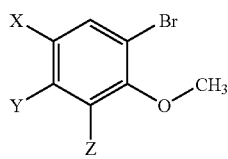

(2)

in which X, Y and Z are as defined for the compound of formula (1), to the action of a halide Hal-$R^2$, where Hal represents a halogen atom, and $R^2$ is as defined for the compound of formula (1), or alternatively of an alcohol OH—$R^2$, with $R^2$ as defined for the compound of formula (1), in the presence of a phosphine, in order to obtain the intermediate of formula (8):

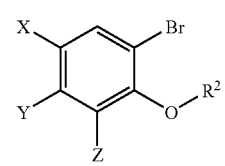

(8)

in which $R^2$, X, Y and Z are as defined for the compound of formula (1), and then by substituting the bromine atom, under the action of an organometallic agent of formula (9):

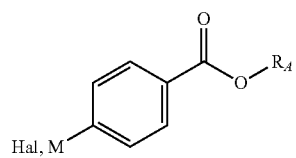

(9)

in which Hal represents a halogen atom, M represents a metal and $R_A$ represents a linear or branched alkyl radical containing 1 to 4 carbon atoms, in order to give a compound of formula (7):

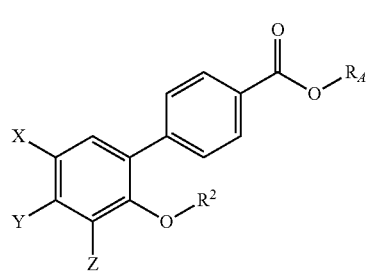

(7)

in which R², X, Y and Z are as defined for the compound of formula (1), and R_A is as defined above, the protecting group R_A of which is then removed to give an acid of formula (1_OH):

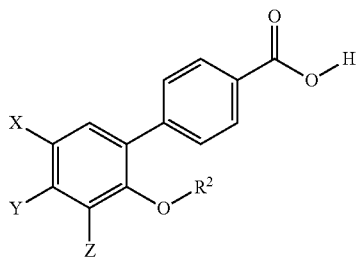

(1_OH)

which is a special case of the compounds of the formula (1) in which R¹ represents a hydroxyl radical, and the acid is optionally esterified, or converted into a corresponding amide to form a compound of formula (1), with R¹ other than a hydroxyl radical.

10. A pharmaceutical composition comprising a compound of claim 1 and a pharmaceutically acceptable carrier.

11. A method for treating dyslipidaemia, atherosclerosis or diabetes comprising administering to a subject in need thereof an effective amount of a compound of claim 1.

12. A compound according to claim 7, which is
4-[6-(5-methyl-2-phenyloxazol-4-ylmethoxy)-1-oxoindan-5-yl]benzoic acid;
4-[1-oxo-6-(4-trifluoromethylbenzyloxy)indan-5-yl]benzoic acid;
4-[6-(2-fluorobenzyloxy)-1-oxoindan-5-yl]benzoic acid;
5'-methoxy-2'-(5-methyl-2-phenyloxazol-4-ylmethoxy) biphenyl-4-carboxylic acid;
5'-methyl-2'-(5-methyl-2-phenyloxazol-4-ylmethoxy)biphenyl-4-carboxylic acid;
4-[6-(5-methylisoxazol-3-ylmethoxy)-1-oxoindan-5-yl] benzoic acid;
4-[6-(5-methyl-2-phenyl-2H-[1,2,3]triazol-4-ylmethoxy)-1-oxoindan-5-yl]benzoic acid;
4-[1-oxo-6-(2-thiophen-2-ylthiazol-4-ylmethoxy)indan-5-yl]benzoic acid;
4-[6-(5-methyl-3-phenylisoxazol-4-ylmethoxy)-1-oxoindan-5-yl]benzoic acid;
methyl 4-{6-[2-(4-chlorophenyl)thiazol-4-ylmethoxy]-oxoindan-5-yl}benzoate;
4-{6-[2-(4-chlorophenyl)thiazol-4-ylmethoxy]-1-oxoindan-5-yl}benzoic acid;
ethyl 4-[6-(5-methyl-2-phenyloxazol-4-ylmethoxy)-1-oxoindan-5-yl]benzoate;
5'-fluoro-2'-[2-(5-methyl-2-phenyloxazol-4-yl)ethoxy]biphenylcarboxylate;
5'-Fluoro-2'-[2-(5-methyl-2-phenyloxazol-4-yl)ethoxy] biphenylcarboxylic acid; or
one of the following compounds

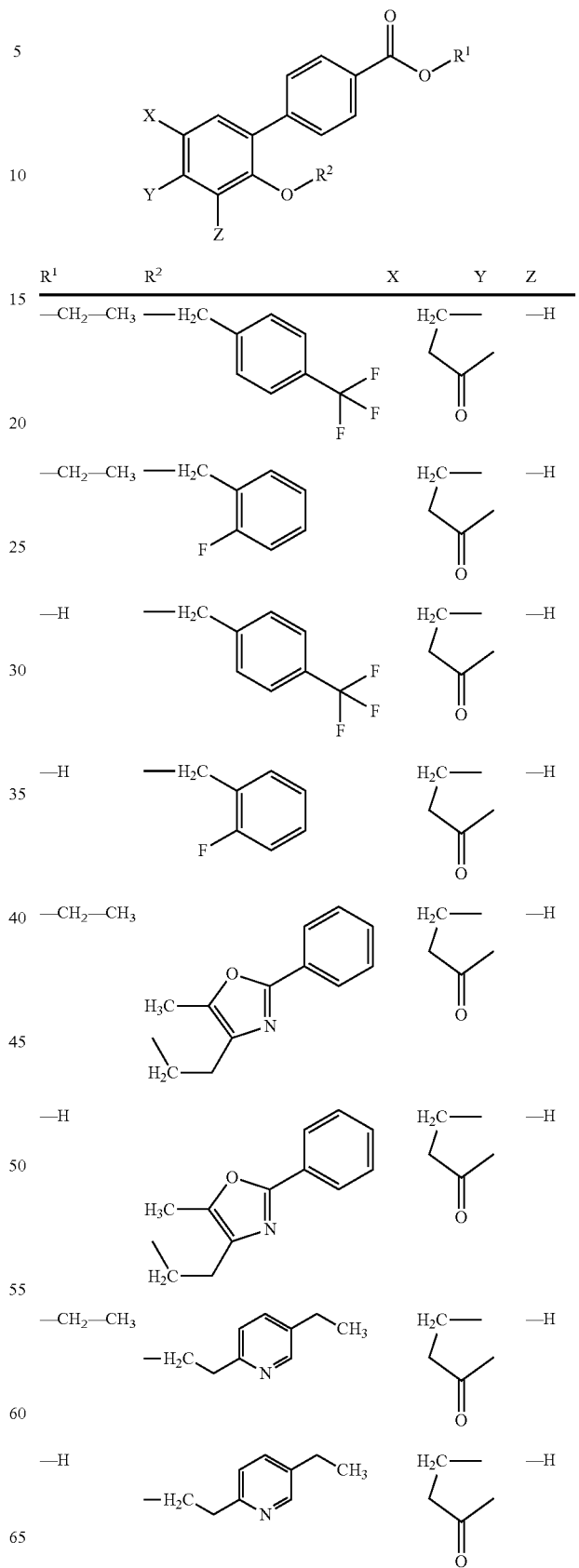

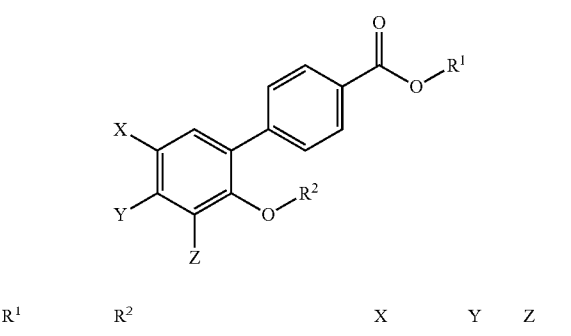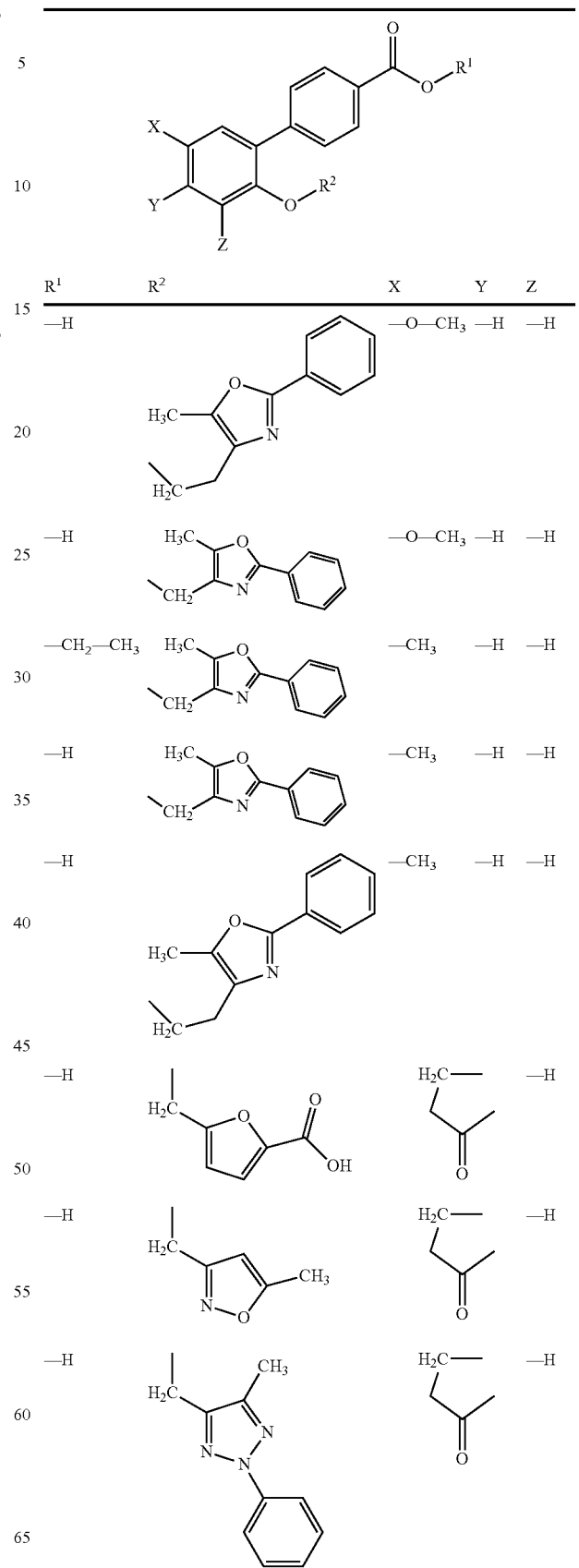

-continued

| R¹ | R² | X | Y | Z |
|---|---|---|---|---|
| —H | 4-(2-thienyl)thiazol-2-ylmethyl | —C(O)CH₂CH₃ | —H | |
| —H | 5-methyl-3-phenylisoxazol-4-ylmethyl | —C(O)CH₂CH₃ | —H | |
| —H | 3-(pyrrol-1-yl)benzyl | —C(O)CH₂CH₃ | —H | |
| —H | 5-tert-butyl-1,2,4-oxadiazol-3-ylmethyl | —C(O)CH₂CH₃ | —H | |
| —H | 5-phenyl-1,2,4-oxadiazol-3-ylmethyl | —C(O)CH₂CH₃ | —H | |
| —H | (3-carboxyfuran-2-yl)methyl | —C(O)CH₂CH₃ | —H | |
| —H | 5-(2-thienyl)-1,2,4-oxadiazol-3-ylmethyl | —C(O)CH₂CH₃ | —H | |

-continued

| R¹ | R² | X | Y | Z |
|---|---|---|---|---|
| —H | 4-(pyrrol-1-yl)benzyl | —C(O)CH₂CH₃ | —H | |
| —H | 5-methyl-2-phenyloxazol-4-ylmethyl | —Cl | —H | —H |
| —H | (5-trifluoromethylfuran-2-yl)methyl | —C(O)CH₂CH₃ | —H | |
| —H | 5-(4-methoxyphenyl)-1,2,4-oxadiazol-3-ylmethyl | —C(O)CH₂CH₃ | —H | |
| —CH₂—CH₃ | 5-methyl-2-phenyloxazol-4-ylmethyl | —F | —H | —F |
| —H | 5-methyl-2-phenyloxazol-4-ylmethyl | —Cl | —H | —H |
| —H | 5-methyl-2-phenyloxazol-4-ylmethyl | —F | —H | —F |
| —CH₂—CH₃ | 5-methyl-2-phenyloxazol-4-ylmethyl | —F | —H | —F |

-continued

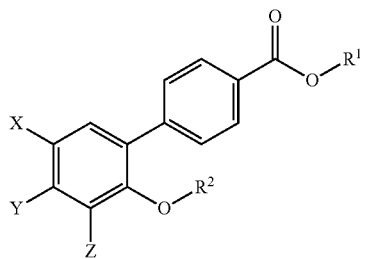

| R¹ | R² | X | Y | Z |
|---|---|---|---|---|
| —H | 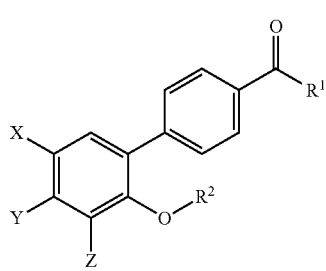 (implied structure 1) | —F | —H | —F |
| —H | (structure 2) | —F | —F | —H |
| —H | (structure 3) | —F | —F | —H | or a pharmaceutically acceptable salt thereof.

13. A method for treating dyslipidaemia, atherosclerosis or diabetes comprising administering to a subject in need thereof an effective amount of a compound of claim 12.

14. A compound according to claim 1, wherein $R^2$ is a butyl, isobutyl, tert-butyl, pentyl, isopentyl, neopentyl, 2-methylbutyl, 1-ethyl-propyl, hexyl, isohexyl, neohexyl, 1-methylpentyl, 3-methylpentyl, 1,1-dimethylbutyl, 1,3-dimethylbutyl, 1-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyloctyl or 7,7-dimethyloctyl group, or an alkenyl or alkynyl radical, or an optionally substituted arylalkyl radical, or an optionally substituted heterocyclylalkyl radical.

15. A compound of the formula (1):

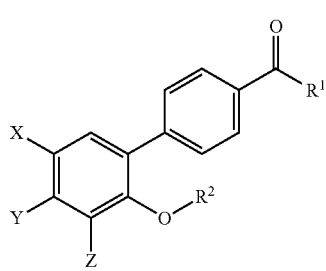

(1)

in which:
$R^1$ represents —O—$R'^1$ or —$NR'^1R'''^1$, with
$R'^1$ and $R'''^1$ are, each independently, a hydrogen atom, an alkyl radical, an alkenyl radical, an alkynyl radical, a cycloalkyl radical, an aryl radical or a heteroaryl radical;
$R^2$ is a propyl, isopropyl, butyl, isobutyl, tert-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 1-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyloctyl or 7,7-dimethyloctyl group, or an alkenyl or alkynyl radical, or an optionally substituted arylalkyl radical, or an optionally substituted heterocyclylalkyl radical;
X and Y are, each independently, a hydrogen atom, a halogen atom, an alkyl radical or an alkoxy radical;
or alternatively
X and Y together form, with the carbon atoms that bear them, a 5-membered ring containing a ketone function; and
Z is a hydrogen atom, a halogen atom, or an alkyl radical;
or a pharmaceutically acceptable salt thereof.

16. A method for treating dyslipidaemia or atherosclerosis comprising administering to a subject in need thereof an effective amount of a compound of claim 1.

17. A compound according to claim 1, wherein
$R^1$ represents —O—$R'^1$ or —$NR'^1R'''^1$, with
$R'^1$ and $R'''^1$ are, each independently, a hydrogen atom, an alkyl radical, an alkenyl radical, an alkynyl radical, a cycloalkyl radical, an aryl radical or a heteroaryl radical;
$R^2$ is a propyl, isopropyl, butyl, isobutyl, tert-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 1-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyloctyl or 7,7-dimethyloctyl group, or an alkenyl or alkynyl radical, or an optionally substituted arylalkyl radical, or an optionally substituted heterocyclylalkyl radical;
X and Y are, each independently, a hydrogen atom, a halogen atom, an alkyl radical or an alkoxy radical;
or alternatively
X and Y together form, with the carbon atoms that bear them, a 5-membered ring containing a ketone function; and
Z is a hydrogen atom, a halogen atom, or an alkyl radical;
or a pharmaceutically acceptable salt thereof.

18. A compound according to claim 7, which is

4-[6-(5-methyl-2-phenyloxazol-4-ylmethoxy)-1-oxoindan-5-yl]benzoic acid;

4-[1-oxo-6-(4-trifluoromethylbenzyloxy)indan-5-yl]benzoic acid;

4-[6-(2-fluorobenzyloxy)-1-oxoindan-5-yl]benzoic acid;

5'-methoxy-2'-(5-methyl-2-phenyloxazol-4-ylmethoxy)biphenyl-4-carboxylic acid;

5'-methyl-2'-(5-methyl-2-phenyloxazol-4-ylmethoxy)biphenyl-4-carboxylic acid;

4-[6-(5-methylisoxazol-3-ylmethoxy)-1-oxoindan-5-yl]benzoic acid;

4-[6-(5-methyl-2-phenyl-2H-[1,2,3]triazol-4-ylmethoxy)-1-oxoindan-5-yl]benzoic acid;

4-[1-oxo-6-(2-thiophen-2-ylthiazol-4-ylmethoxy)indan-5-yl]benzoic acid; or

4-[6-(5-methyl-3-phenylisoxazol-4-ylmethoxy)-1-oxoindan-5-yl]benzoic acid;

or a pharmaceutically acceptable salt thereof.

19. A compound according to claim 1, wherein X and Y together form, with the carbon atoms that bear them, a 5-membered ring containing a ketone function; or Z is a hydrogen atom, a halogen atom, or an alkyl radical.

20. A method for treating type II diabetes comprising administering to a subject in need thereof an effective amount of a compound of claim 1.

21. A method for treating type II diabetes comprising administering to a subject in need thereof an effective amount of a compound of claim 12.

22. A compound according to claim 15, wherein $R^2$ is a pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 1-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyloctyl or 7,7-dimethyloctyl group, or an alkenyl or alkynyl radical, or an optionally substituted arylalkyl radical, or an optionally substituted heterocyclylalkyl radical.

23. A compound according to claim 15, wherein $R^2$ is an alkenyl or alkynyl radical, or an optionally substituted arylalkyl radical, or an optionally substituted heterocyclylalkyl radical.

24. A compound according to claim 15, wherein $R^2$ is an optionally substituted arylalkyl radical, or an optionally substituted heterocyclylalkyl radical.

25. A compound according to claim 15, wherein $R^2$ is an optionally substituted benzyl radical, or an optionally substituted heterocyclylalkyl radical, wherein the substituents of the radicals of the compounds of the formula (1) are a halogen atom, or a methyl, ethyl, methoxy, phenyl, trifluoromethyl or a trifluoromethoxy group, wherein the heterocyclic radicals are selected from the group consisting of furyl, thienyl, pyrrolyl, pyridyl, triazolyl, oxazolidinyl, thiazolyl, oxadiazolyl and oxazolyl radicals.

26. A compound according to claim 15, wherein X and Y together form, with the carbon atoms that bear them, a 5-membered ring containing a ketone function.

27. A compound according to claim 15, wherein Z is hydrogen or fluorine.

28. A compound according to claim 15, wherein X or Y is halogen.

* * * * *